(12) United States Patent
Lauber et al.

(10) Patent No.: US 12,158,472 B2
(45) Date of Patent: *Dec. 3, 2024

(54) METHODS FOR THE RAPID PREPARATION OF LABELED GLYCOSYLAMINES AND FOR THE ANALYSIS OF GLYCOSYLATED BIOMOLECULES PRODUCING THE SAME

(71) Applicant: Waters Technologies Corporation, Milford, MA (US)

(72) Inventors: Matthew A Lauber, North Smithfield, RI (US); Darryl W. Brousmiche, Grafton, MA (US); Stephan M. Koza, Lancaster, MA (US)

(73) Assignee: Waters Technologies Corporation, Milford, MA (US)

( * ) Notice: Subject to any disclaimer, the term of this patent is extended or adjusted under 35 U.S.C. 154(b) by 261 days.

This patent is subject to a terminal disclaimer.

(21) Appl. No.: 17/741,865

(22) Filed: May 11, 2022

(65) Prior Publication Data
US 2022/0268779 A1 Aug. 25, 2022

Related U.S. Application Data

(63) Continuation of application No. 15/522,908, filed as application No. PCT/US2015/057848 on Oct. 28, 2015, now Pat. No. 11,371,996.

(60) Provisional application No. 62/107,994, filed on Jan. 26, 2015, provisional application No. 62/072,747, filed on Oct. 30, 2014.

(51) Int. Cl.
*C12P 19/28* (2006.01)
*G01N 33/58* (2006.01)
*G01N 33/68* (2006.01)

(52) U.S. Cl.
CPC .............. *G01N 33/58* (2013.01); *C12P 19/28* (2013.01); *G01N 33/582* (2013.01); *G01N 33/6842* (2013.01); *G01N 2333/924* (2013.01); *G01N 2333/98* (2013.01); *G01N 2440/38* (2013.01)

(58) Field of Classification Search
CPC ....................................................... C12P 19/28
See application file for complete search history.

(56) References Cited

U.S. PATENT DOCUMENTS

| | | | |
|---|---|---|---|
| 2,016,962 A | 10/1935 | Flint et al. | |
| 4,003,912 A | 1/1977 | Franz | |
| 4,068,528 A | 1/1978 | Gundelfinger | |
| 4,138,398 A | 2/1979 | Richter et al. | |
| 5,296,599 A | 3/1994 | Cohen et al. | |
| 5,531,959 A | 7/1996 | Johnson et al. | |
| 5,696,599 A | 12/1997 | Tiso | |
| 6,245,478 B1 | 6/2001 | Uetani et al. | |
| 6,379,971 B1 | 4/2002 | Schneider et al. | |
| 6,632,629 B2 | 10/2003 | Yang et al. | |
| 6,716,634 B1 | 4/2004 | Myerson | |
| 7,074,570 B2 | 7/2006 | Palmgren et al. | |
| 7,148,069 B2 | 12/2006 | Miyano et al. | |
| 7,186,739 B2 | 3/2007 | Guichard et al. | |
| 7,494,815 B2 | 2/2009 | Shimbo et al. | |
| 7,732,378 B2 | 6/2010 | Thompson et al. | |
| 8,124,792 B2 | 2/2012 | Baginski | |
| 8,198,063 B1 | 6/2012 | Baginski et al. | |
| 8,445,292 B2 | 5/2013 | Baginski | |
| 9,658,234 B2 | 5/2017 | Miyano et al. | |
| 10,416,166 B2 | 9/2019 | Brousmiche et al. | |
| 11,371,996 B2 * | 6/2022 | Lauber ................ | G01N 33/582 |
| 2001/0026929 A1 | 10/2001 | Yang et al. | |
| 2004/0259262 A1 | 12/2004 | Ishii | |
| 2005/0079624 A1 | 4/2005 | Miyano et al. | |

(Continued)

FOREIGN PATENT DOCUMENTS

| | | |
|---|---|---|
| CN | 1211622 A | 3/1999 |
| CN | 1973047 A | 5/2007 |

(Continued)

OTHER PUBLICATIONS

European Search Report for Application No. 15855907.0, mailed on Jul. 6, 2018 , 12 pages.
Expert Declaration by Prof. Ulf Diederichsen dated Jul. 23, 2019, 7 pp.
Extended European Search Report and Written Opinion for EP Application No. 15855907.0 dated Mar. 19, 2018, 10 pages.
Extended European Search Report for Application No. 17767589.9, dated Jan. 30, 2020, 11 pages.
Extended European Search Report for Application No. EP17820918. 5, dated Jan. 28, 2020, 7 pages.
Extended European Search Report for Application No. EP20188814. 6, dated Oct. 2, 2020, 7 pages.
Extended European Search Report for EP Application No. 17815987. 7, mailed on Dec. 16, 2019, 8 pages.

(Continued)

*Primary Examiner* — Ruth A Davis
(74) *Attorney, Agent, or Firm* — WOMBLE BOND DICKINSON (US) LLP; Deborah M. Vernon; Ricardo Joseph

(57) ABSTRACT

Methods of analyzing glycosylated biomolecules include the steps of producing a deglycosylation mixture of biomolecules deglycosylated by natural or synthetic enzymatic or chemical techniques; providing a reagent solution having a labeling reagent in a polar aprotic, non-nucleophilic organic solvent; and mixing the deglycosylation mixture with the reagent solution in an excess of labeling reagent to produce derivatized glycosylamines. The method steps can be carried out purposefully without depletion of protein matter. A quenching solution can be added to the reaction mixture so that the pH of the reaction mixture is shifted to above 10. The yield of derivatized glycosylamines can be in an amount of about 80 to about 100 mole percent of the reaction mixture with minimal overlabeling, less than 0.2 mole percent. The derivizated glycosylamines can be separated from the reaction mixture and detected by chromatographic detection, fluorescence detection, mass spectrometry ("MS"), or Ultra Violet ("UV") detection and/or a combination thereof.

16 Claims, 27 Drawing Sheets

(56) References Cited

U.S. PATENT DOCUMENTS

| | | |
|---|---|---|
| 2005/0158708 A1 | 7/2005 | Alroy et al. |
| 2005/0221337 A1 | 10/2005 | Seeberger et al. |
| 2006/0004220 A1 | 1/2006 | Hamprecht et al. |
| 2006/0035304 A1 | 2/2006 | Lebrilla et al. |
| 2006/0127950 A1 | 6/2006 | Bosques et al. |
| 2006/0286673 A1 | 12/2006 | Miyano et al. |
| 2007/0141723 A1 | 6/2007 | Sompuram et al. |
| 2007/0269895 A1 | 11/2007 | Aebersold et al. |
| 2008/0201095 A1 | 8/2008 | Yip et al. |
| 2008/0241856 A1 | 10/2008 | Wong et al. |
| 2008/0315084 A1 | 12/2008 | Yamada et al. |
| 2009/0050212 A1 | 2/2009 | Dourdeville et al. |
| 2009/0065687 A1 | 3/2009 | Gross et al. |
| 2009/0258437 A1 | 10/2009 | Baginski |
| 2010/0151499 A1 | 6/2010 | Collins et al. |
| 2010/0171055 A1 | 7/2010 | Dourdeville |
| 2011/0006237 A1 | 1/2011 | Tower |
| 2011/0171736 A1 | 7/2011 | Agnew et al. |
| 2012/0107942 A1 | 5/2012 | Baginski |
| 2012/0165370 A1 | 6/2012 | Tang et al. |
| 2013/0112604 A1 | 5/2013 | Keene et al. |
| 2013/0171658 A1 | 7/2013 | Fulton et al. |
| 2014/0030732 A1 | 1/2014 | Staples |
| 2014/0038215 A1 | 2/2014 | Smart et al. |
| 2014/0178912 A1 | 6/2014 | Liu et al. |
| 2014/0179011 A1 | 6/2014 | Brousmiche et al. |
| 2014/0200148 A1 | 7/2014 | Slade |
| 2014/0227793 A1 | 8/2014 | Gao et al. |
| 2014/0274768 A1 | 9/2014 | Haab |
| 2014/0350263 A1 | 11/2014 | Brousmiche et al. |
| 2014/0352063 A1 | 12/2014 | Mitchell et al. |
| 2014/0370614 A1 | 12/2014 | Liu et al. |
| 2015/0057243 A1 | 2/2015 | Zhou et al. |
| 2015/0204824 A1 | 7/2015 | Lauber et al. |
| 2015/0346194 A1 | 12/2015 | Magnelli et al. |
| 2016/0018409 A1 | 1/2016 | Higel |
| 2016/0054274 A1 | 2/2016 | Cormier et al. |
| 2016/0069844 A1 | 3/2016 | Jackson et al. |
| 2016/0139136 A1 | 5/2016 | Brousmiche et al. |
| 2017/0370813 A1 | 12/2017 | Steen et al. |

FOREIGN PATENT DOCUMENTS

| | | |
|---|---|---|
| CN | 102690833 A | 9/2012 |
| CN | 103842818 A | 6/2014 |
| CN | 103877748 A | 6/2014 |
| CN | 103918055 A | 7/2014 |
| CN | 104024849 A | 9/2014 |
| EP | 0533200 A1 | 3/1993 |
| EP | 0671401 A1 | 9/1995 |
| EP | 1475632 A1 | 11/2004 |
| EP | 1750126 A1 | 2/2007 |
| EP | 2305692 A1 | 4/2011 |
| EP | 2990401 A1 | 3/2016 |
| JP | S59161355 A | 9/1984 |
| JP | S60186502 A | 9/1985 |
| JP | S62195361 A | 8/1987 |
| JP | H09101310 A | 4/1997 |
| JP | H10306075 A | 11/1998 |
| JP | H1180107 A | 3/1999 |
| JP | 2000510854 A | 8/2000 |
| JP | 2000329744 A | 11/2000 |
| JP | 2003194799 A | 7/2003 |
| JP | 2006038674 A | 2/2006 |
| JP | 2006523305 A | 10/2006 |
| JP | 2008539413 A | 11/2008 |
| JP | 2012512234 A | 5/2012 |
| JP | 2013142566 A | 7/2013 |
| JP | 2014534176 A | 12/2014 |
| JP | 2015091953 A | 5/2015 |
| WO | 199921580 A1 | 5/1999 |
| WO | 199929897 A1 | 6/1999 |
| WO | 2002074245 A2 | 9/2002 |
| WO | 200306328 A1 | 1/2003 |
| WO | 2004027388 A2 | 4/2004 |
| WO | 2004086050 A2 | 10/2004 |
| WO | 2005116629 A1 | 12/2005 |
| WO | 2006114663 A1 | 11/2006 |
| WO | 2007069591 A1 | 6/2007 |
| WO | 2009070233 A1 | 6/2009 |
| WO | 2009100155 A1 | 8/2009 |
| WO | 2009158034 A1 | 12/2009 |
| WO | 2011038873 A1 | 4/2011 |
| WO | 2011146594 A2 | 11/2011 |
| WO | 2013025527 A1 | 2/2013 |
| WO | 2013049622 A1 | 4/2013 |
| WO | 2013081581 A1 | 6/2013 |
| WO | 2013084236 A1 | 6/2013 |
| WO | 2013151975 A1 | 10/2013 |
| WO | 2013192530 A2 | 12/2013 |
| WO | 2014085938 A1 | 6/2014 |
| WO | 2014194320 A1 | 12/2014 |
| WO | 2016009077 A1 | 1/2016 |
| WO | 2016069764 A1 | 5/2016 |
| WO | 2016089515 A1 | 6/2016 |

OTHER PUBLICATIONS

Extended European Search Report, EP 12836127.6, Aug. 26, 2014.

Fekkes, "State-Of-The-Art of High-Performance Liquid Chromatographic Analysis of Amino Acids in Physiological Samples," Journal Chromatography B. 682(1):3-22 (1996).

Field, B., et al., Chromatography Forum: LC-MS & GC-MS Archives: AAA LC-MS [online] 2003 [retrieved on Jan. 30, 2003]. Retrieved from Internet URL: http://www.lcresources.com/dscus/messages/5135/3143.html, 6 pages.

Fu-Chuan, Li, et al., "Studies on Fluorescent Labeling of Marine Sulfated Polysaccharide 911", Chemical Journal of Chinese Universities, 23(9): 1704-1708 (2002).

GlykoPrep™ Instant AB now fully commercialized [online] Mar. 2011 [retrieved on Sep. 13, 2020]. Retrieved from ntemet URL: web.archive.org/web/20120115033552/http://www.europa-bioproducts.com/latesl/aspx?id=14.

GlykoPrep™ Instant AB now fully commercialized. http://www.eropa-bioproducts.com/latest.aspx?id=14 (Accessed Sep. 8, 2014).

Gong et al., N-Glycosylamine-Mediated Isotope Labeling for Mass Spectrometry-Based Quantitative Analysis of N-Linked Glycans. Anal Bioanal Chem 2013; 405: 5825-31.

Guichard, G., et al., "Effective Preparation of O-Succinimidyl-2-(lert-Butoxycarbonylamino) ethylcarbamale Derivatives from Bela-Amino Acids. Application to the Synthesis of Urea-Containing Pseudopeplides and Oligoureas", Journal of Org Chem 64:8702-8705 (1999).

Guile G. R., et al., "A Rapid High-Resolution High-Performance Liquid Chromatographic Method for Separating Glycan Mixtures and Analyzing Oligosaccharide Profiles," Analytical Biochemistry, 240: 210-226, (1996).

Harvey et al., Electrospray Mass Spectrometry and Fragmentation of N-Linked Carbohydrates Derivatized at the Reducing Terminus, J Am Soc Mass Spectrom 2000, 11 (10), 900-15.

Harvey et al., Proposal for a standard system for drawing structural diagrams of N- and O-linked carbohydrates and related compounds, Proteomics 2009; 9 (15): 3796-801.

Harvey, D., "Identification of protein-bound carbohydrates by mass spectrometry" Proteomics 1:311-328 (2001).

Harvey, D.J., "Derivatization of carbohydrates for analysis by chromatography: electrophoresis and mass spectrometry", Journal of Chromatography B 879(17-18): 1196-1225 (2011) Abstract.

Heindel, N.D., et al., "Diaminoquinoline antimalarials", J. Med. Chem. 12(5):797-801 (1969).

Heinze-Krauss, I., et al., "Structure-Based Design of B-Lactamase Inhibitors. 1. Synthesis and Evaluation of Bridged Monobactams", Journal of Med Chem 41:3961-3971 (1998) Abstract.

Hermanson, "Bioconjugate Techniques," (1996) Academic Press, Chapter 8. Abstract.

Higashi, T., et al., "Derivatization of Neutral Steroids to Enhance Their Detection Characteristics in Liquid Chromatography-Mass Spectrometry", Anal Bioanal Chem 378:875-882 (2004).

(56) References Cited

OTHER PUBLICATIONS

Higuchi, K., et al., "Chemistry of Succinimido Esters. IV*1. A Facile Preparation of N-Succinimidyl Carboxylates Using N, N'-Disuccinimidyl Carbonate", Oil Chemistry, 36(1):16-20 (1987).
Hirai, "Development of a new fluorescence labeling reagent succinimido-2-fluorenylcarbamate for highly sensitive detection of Nsolanesyl-N,N-bis(3,4-dimethoxybenzyl)ethanediamine by HPLC," Anal. Chem. 1991, 10(5), 233-238. Abstract.
Hochleitner, E.O., et al., "Determination of the Stoichiometry of Protein Complexes Using Liquid Chromatography with fluorescence and Mass Spectrometric Detection of Fluorescently Labeled Proteolytic Peptides", Proteomics 1:669-676 (2004).
Holmes et al. "Solid-Phase Synthesis of Artificial beta-Sheets" Journal of American Chemical Society 119: 7665-7669 (1997).
Hossler et al., "Optimal and Consistent Protein Glycosylation in Mammalian Cell Culture", Glycobiology 19(9):936-949 (2009).
HP Primer Hewlett Packard, Basics of LC/MS: A Primer. 1998.
Huang, R., ed., Analytical Chemistry, National Defense Science and Technology University Press pp. 146-150 (Mar. 2014).
International Preliminary Report on Patentability, for International application No. PCT/US2012/057996, Apr. 1, 2014.
International Search Report and Written Opinion for International Application No. PCT/US 171038073, mailed on Sep. 12, 2017, 9 pages.
International Search Report and Written Opinion for International application No. PCT/US15/60326, Feb. 2, 2016, pages.
International Search Report and Written Opinion for PCT/GB2016/051605 mailed Sep. 15, 2016.
International Search Report and Written Opinion, 02/05/20126. International App. No. PCT/US15/57848.
International Search Report and Written Opinion for International Application No. PCT/US2017/038070, mailed on Sep. 29, 2017, 10 pages.
International Search Report and Written Opinion, Apr. 27, 2017, for International Application No. PCT/US2017/014790, 6 pages.
International Search Report and Written Opinion, for International application No. PCT/US2012/057996 mailed Jan. 31, 2013, 8 pages.
Isbell, H.S. et al., "Effect of pH in the Mutarotation and Hydrolysis of Glycosylamines", JAGS letter to editor, 72:1043-1044 (1950).
Itnernational Search Report and Written Opinion for International Application No. PCT/US2017/038072, mailed on Oct. 3, 2017, 9 pages.
Iwaki, "Activated carbamate reagent as chiral derivatizing agent for liquid chromatographic optical resolution of enantiomeric amino compounds," Chromatographia 1987, 23(12), 899-902 Abstract.
Iwaki, "Amino acid analysis by reversed-phase high-performance liquid chromatography. Automatic pre-column derivatization with activated carbamate reagent", Journal of Chromatography, 407 (1987) 273-279 Abstract.
Johannesen et al. "Glycan analysis via derivatization with a fluorogenic pyrylium dye." Carbohydrate Res. 352(2012):94-100.
Jupille, "UV-Visible Absorption Derivatization in Liquid Chromatography," Journal of Chromatographic Science 1979, 17:160-167. Abstract.
Kimzey, Michael et al., "Development of an Instant Glycan Labeling Dye for High Throughput Analysis by Mass Spectrometry", Prozyme Advancing Glycosciences, May 13, 2015, 4 pages.
Kinzel et al. "Identification of MK-5710 ((8aS)-8a-methyl-1,3-dioxo--[(1S,2R)-2-phenylcyclopropyl]-N-(1-phenyl-1 H-pyrazol-5-yl)hexahydro-imidazo[1,5-a]pyrazine-7 (1 H)-carboxamide), a potent smoothened antagonist for use in Hedgehog pathway dependent malignancies, Part 2." Bioorg. Med. Chem. Lett. 21(2011): 4429-4435.
Klapoetke et al., The evaluation of a novel approach for the profiling and identification of N-linked glycan with a brocainamide tag by HPLC with fluorescent and mass spectrometric detection, J Pharm Biomed Anal 2010; 53 (3): 315-24.
Klapoetke, S, et al., "The Evaluation of a Novel Approach for the Profiling and Identification of N-linked Glycans With a Procainamide Tag by HPLC With Fluorescent and Mass Spectrometric Detection", Journal of Pharmaceutical and Biomedical Analysis 53(3):315-324 ( 2010).
Knezevic, A., et al., "High throughput plasma N-glycome profiling using multiplexed labelling and UPLC with uorescence detection", Analyst, 136:4670 (2011 ).
Kurita, K., et al., "Synthesis and Properties of Polyurethanes Derived from bis-N-Hydroxyimides and Diisocyanales", Journal of Polymer Science 17:1619-1629 (1979).
Kuster et al. "Structural Determination of N-linked carbohydrates by matrix-assisted laser desorption/ionization mass spectrometry following enzymatic release within sodium dodecyl sulphate-polyacrylamide electrophoresis gels: application to species-species glycosylat." Electrophoresis. 19.11(1990): 1950-1959.
Lauber, Matthew A., Stephan M. Koza, and Kenneth J. Fountain. "Optimization of GlycoWorks HILIC SPE for the quantitative and robust recovery of N-linked glycans from mAb-type samples." Waters Application Note, 720004717EN (2013).
Lauber, M.A. et al., "Rapid Preparation of Released N-Glycans for HILIC Analysis Using a Labeling Reagent that Facilitiates Sensitive Fluorescence and ESI-MS Detection", Analytical Chemistry 87:5401-5409 (2015).
Lawrence, "Derivatization in Chromatography Introduction, Practical Aspects of Chemical Derivatization in :; hromatography," Journal of Chromatographic Science 1979, 17:113-114. Abstract.
Li De et al., "Techniques of Biomolecule Scientific Experiments", Hunan Science and Technology Press, November of 2001, the 1st edition, p. 32-33.
Liang, et al., "Quantitative determination of endogenous sorbitol and fructose in human nerve tissues by atmospheric- pressure chemical ionization liquid chromatography tandem mass spectrometry", Rapid Communications Mass Spectrometry, 19(16):2284-2294, Aug. 30, 2005. Abstract.
Liu et al. Investigation of Sample Preparation Artifacts Formed during the Enzymatic Release of N-Linked Glycans prior to Analysis by Capillary Electrophoresis. Anal. Chem. 2009; 81: 6823-6829.
Liu, H., et al., "Determination of Submicromolar Concentrations of Neurotransmitter Amino Acids by Fluorescence Detection Using a Modification of the 6-Aminoquinolyl-N-Hydroxysuccinimidyl Carbamate Method for Amino Acid Analysis", Journal of Chromatograpjy A, 828:383-395 (1998).
Liu, H., et al., "Femtomole Peptide Mapping by Derivatization, High-Performance Liquid Chromatography, and Fluorescence Detection", Analytical Biochemistry 294:7-18 (2001) CNOA for application 201580071764.2 dated Feb. 28, 2020 original and translated document, 18 pages.
Liu, Hongji, et.al .; "Homogeneous Fluorescent Derivatization of Large Proteins", Journal of Chromatography A, 927: 77-89 (2001) Abstract.
Louris, "New Scan Modes Accessed with a Hybrid Mass Spectrometer," Anal. Chem. 1985, 57, 2916-2924. Abstract.
Marino et al., "A Systematic Approach to Protein Glycosylation Analysis: A Path Through the Maze", Nature Chemical Biology 6:713-723 (2010) Abstract.
Martinez-Force, E., et al., "Separation of O-Phthalaldehyde Derivatives of Amino Acids of the Internal Pool of Yeast by Reverse-Phase Liquid Chromatography", Biotechnology Technique 5(3):209-214 (1991) Abstract.
Mazzocchi, Paul et al., "A Photochemical Route to Pyrrolo[1,4] Benzodiazepine Antitumor Antibiotics" Heterocycles 23(7):1603-1606 (1985).
Mechref et al., Quantitative Glycomics Strategies, Mol Cell Proteomics 2013, 12 (4) 874-84.
Morpugo, "N-hydroxysuccinimide carbonates and carbamates are useful reactive reagents for coupling ligands to ysines on proteins," J. Biochem. Biophys. Methods 38 (1999), 17-28.
Nakashima, "Study on P-P Interaction in High Performance Liquid Chromatography," J. Liq. Chrom. & Rel. Technol. 2000, 23(16), 2533-2540. Abstract.
Neville, D.C.A., et al., "Development of a Single col. Method for the Separation of Lipid- and Protein-Derived Oligosaccharides", Journal of Proteome Research, 8(2):681-687 (2009).

(56) References Cited

OTHER PUBLICATIONS

Nimura, "Detection reagents used for high performance liquid chromatography," Pharmacia (1981) 17(8):707-709.

Nimura, N., et al., "Activated Carbamate Reagent as Derivatizing Agent for Amino Compounds in High-Performance Liquid Chromatography", Analytical Chemistry 58:2372-2375 (1986).

Non-Final Office Action, U.S. Appl. No. 14/193,418, dated Nov. 15, 2016.

Non-Final Office Action, U.S. Appl. No. 14/342,131, dated Nov. 4, 2016.

Notice for Reasons for Rejection, dated Jul. 23, 2012, in Japanese Application No. 2009-269796, original and translated documents.

Notice of Rejection, JP Application No. 2014-533416, dated Jan. 10, 2017. Original and translated.

Office Action, U.S. Appl. No. 14/458,760, dated Apr. 12, 2017.

Okamoto, Sensitive Detection and Structural Characterization of Trimethyl(p-aminophenyl)-ammonium-derivatized Oligosaccharides by Electrospray Ionization-Mass Spectrometry and Tandem Mass Spectrometry,11 Rapid Communications in Mass Spectrometry, 1995, 9, 641-643. Abstract.

Pall Life Sciences "AcroPrep Advance Filler Plates" Pall Corporation (Mar. 2013) p. 7, col. 2, 10 Table AcroPrep Advance 96-Well Filler Plates for Ultrafillralion.

Park, S., et al., "Regioselective Covalent Modification of Hemoglobin in Search of Antisickling Agents", J Med Chem 16:936-953 (2003) Abstract.

Paschinger, K., et al., "Analysis of zwillerionic and anionic N-linked glycans from invertebrates and protisls by mass spectrometry", Glycoconjugate Journal, 33(3):273-283 (2016).

Pettersson et al., Chemical Stability of Reversed Phase High Performance Liquid Chromatography Silica under Sodium Hydroxide Regeneration Conditions, J Chromatogr A 2007; 1142 (1 ): 93-7.

Piepponen et al. "Rapid and Sensitive Step Gradient Assays of Glutamate, Glycine, Taurine and y-Aminobutyric Acid by High-Performance Liquid Chromatography-Fluorescence Detection with o-Phthalaldehyde_mecaptoethanol Derivation With an Emphasis on Microdialysis Samples." J. Chromatogr. B. 757(2001): 277-283.

Pubchem CID: 43450869 Create Dale: Jul. 21, 2009.

Qu, Y., et al., "Structural analysis of N- and O-glycans using ZIC-HILIC/dialysis coupled to NMR detection", Fungal Genetics and Biology, 72:207-215 (2014).

Quirke, "Chemical Derivatization for Electrospray Ionization Mass Spectrometry. 1. Alkyl Halides, Alcohols, Phenols, Thiols, and Amines", Anal Chem. 1994, 66, 1302-1315. Abstract.

Rasmussen, "The nomenclature of fused-ring arenes and heterocycles: a guide to an increasingly important dialect of Organic chemistry," ChemTexts, 2016, 2(16), 1-13.

Registry File from STN for compound RN 1915940-97-4, entered on STN May 23, 2016, downloaded Sep. 8, 2020 {Year: 2016).

Registry File from STN for compound RN 1919202-16-6, entered on STN May 27, 2016, downloaded Sep. 8, 2020 {Year: 2016).

Registry File from STN for compound RN 1970079-84-5, entered on STN Aug. 9, 2016, downloaded Sep. 8, 2020 {Year: 2016).

Registry File from STN for compound RN 1975675-34-3, entered on STN Aug. 19, 2016, downloaded Sep. 8, 2020 {Year: 2016).

Registry File from STN for compound RN 1977407-60-5, entered on STN Aug. 22, 2016, downloaded Sep. 8, 2020 {Year: 2016).

Response to EP Communication with extended search report, EP Application No. 15180680.9, dated Sep. 2, J016.

Response to Non-Final Office Action, U.S. Appl. No. 14/342,131 dated Feb. 6, 2017.

Response to Non-Final Office Action, U.S. Appl. No. 14/193,418, dated Feb. 15, 2017.

Response to notice of opposition for EP Patent No. 2761296 filed Oct. 19, 2018.

Response to Office Action, U.S. Appl. No. 14/458,760, dated Jun. 12, 2017.

Response to Restriction Requirement, U.S. Appl. No. 14/342,131 dated Sep. 28, 2016.

Restriction Requirement, U.S. Appl. No. 14/342,131, dated Aug. 17, 2016.

Reubsaet, "Characterisation of TT-TT interactions which determine retention of aromatic Compounds in reversed- phase liquid chromatography," Journal of Chromatography A, 1999, 841, 147-154. Abstract.

Roth, "Charge Derivatization of Peptides For Analysis By Mass Spectrometry," Mass Spectrometry Reviews 1998, 17:255-274 Abstract.

Ahn J., et al., "Separation of 2-aminobenzamide labeled glycans using hydrophilic interaction chromatography columm backed with 1. 7 Aµm sorbent," Journal of Chromatography B, 878: 403-8 (2010).

Amendment and Response filed Feb. 4, 2009 in response to Office Action mailed Jun. 30, 2011, in U.S. Appl. No. 12/365,880.

Anumula et al., "High Resolution and High Sensitivity Methods for Oligosaccharide Mapping and Characterization by Normal Phase High Performance Liquid Chromatography Following Derivitization with Highly Flourescent Anthranilic Acid", Glycobiology 8(7):685-694 (1998).

Author unknown, Best Practices in the Analysis of Rapifluor-MS Labeled Glycans Using the Acquity QDa Detector 5 Performance Model), Waters [online] Mar. 2016 While Paper [retrieved on Apr. 1, 2020]. Retrieved from the nlernel URL: https://www.gimitec.com//file/720005655en.pdf, 19 pages.

Bartlet-Jones, "Peptide ladder sequencing by mass spectrometry using a novel, volatile degradation reagent," Rapid Commun. Mass Spectrom. 1994, 8, 737-742. Abstract.

Bereman et al., Increasing the hydrophobicity and electrospray response of glycans through derivatization with hovel cationic hydrazides, Chem Commun (Camb) 2010; 26 (2): 237-9.

Bioengineering Analysis and Inspection, Wang Furong China Light Industry Press pub. Jun. 30, 2005.

Black, S.D., et al., "Simple, Rapid, and Highly Efficient Separation of Amino Acid Phenylthiohydantoins by Reversed- Phase High-Performance Liquid Chromatography", Analytical Biochemistry 121:281-285 (1982).

Block et al., "2050P: Hplc/Ms Analysis of Amino Acids: The Use of 6-Aminoquinolyl-N-Hydroxy-Succinimidyl Carbamate Derivatives", Poster presented at Pittsburgh Conference, Mar. 1999.

Block, E.H., "LC/MS Application Notes: The Use of 6-Aminoquinolyl N Hydroxy Succinimidyl Carbamate Derivatives for HPLC/MS Analysis of Amino Acids", Presentation at Pittsburgh Conference, Mar. 1999.

Block, E.H., "The Use of 6-Aminoquinolyl-N-Hydroxy Succinimidyl Carbamate Derivatives for HPLC/MS Analysis of Amino Acids", AMD35 Waters Alliance LC/MS System 2000.

Brancia, Improved matrix-assisted laser desorption/ionization mass spectrometric analysis of tryptic hydrosylates of proteins following guanidation of lysinecontaining Commun. Mass Spectrom. 14, 2070-2073 (2000) Abstract.

Briggs, J.B., et al., "An analytical system for the characterization of highly heterogeneous mixtures of N-linked oligosaccharides", Analytical Biochemistry, 389:40-51 (2009).

Brophy, "Electron Impact and chemical ionization mass spectra of aryl ureas," Organic Mass Spectrometry, vol. 14, No. 7, 1979, 379-386 Abstract.

Bunz, S-C., et al., "Analysis of native and APTS-labeled N-glycans by capillary electrophoresis/time-Of-flight mass spectrometry", Analytical and Bioanalytical Chemistry 405:8277-8284 (2013).

Busto, "Solid phase extraction of biogenic amines from wine before chromatographic analysis of their AQC Deriviatives" Liq. Chrom. & Rel. Technol. 1997, 20(5), 743-755 Abstract.

Byrnes, "6-Aminoquinoline as a Fluorogenic Leaving Group in Peptide Reactions: A New Fluorogenic Substrate for Chymotrypsin," Anal. Biochem. 116, 408-413 (1981) Abstract.

Campbell M. P., et al., "GlycoBase and autoGU: tools for HPLC-based glycan analysis," Bioinformatics, 24 (9): 1214-1216, (2008).

Casoli, A., et al., "Use of High-Performance Liquid Chromatography For the Determination of Amino Acids in Sparkling Nines", Am J Enol Vitic 33(3):135-139 (1982).

Chapter 2—Norepinephrine cited during EP3472132 examination procedure Jul. 16, 2020.

(56) References Cited

OTHER PUBLICATIONS

Chezal, J.-M., et al. "Evaluation of Radiolabeled {Hetero) Aromatic Analogues of N-{2-diethylaminoethyl)-4-lodobenzamide for Imaging and Targeted Radionuclide Therapy of Melanoma" J. Med. Chem. 51:3133-3144 (2008).
Ciucanu et al., A Simple and Rapid Method for the Permethylation of Carbohyrates, Carbohydr. Res. 1984, 131, 209-217.
Cline et al., "The Aminolysis of N-Hydroxysuccinimide Esters. A Structure-Reactivity Study", J Am Chem Soc 109(10):3087-3091 (1987).
CNOA for application 201580071764.2 dated Feb. 28, 2020 original and translated document, 18 pages.
CNOA for Patent Application No. 201780053453.2 dated Feb. 4, 2021, original and translated document 24 pages.
Cohen, "Clearing the Hurdle of High Sensitivity in Biopharmaceutical Research," LCGC North America 1999, 17(4S):S9-S16.
Cohen, S. A., et al., "Compositional Protein Analysis Using 6-Aminoquinolyl-N-Hydroxysuccinimidyl Carbamale, a Novel Derivatization Reagent", Techniques in Protein Chemistry IV, pp. 289-298 (1993).
Cohen, S. A., et al., "Synthesis of a Fluorescent Derivatizing Reagent, 6-Aminoquinolyl-N-Hydroxysuccinimidyl Carbamate, and Its Application for the Analysis of Hydrolysate Amino Acids via High-Performance Liquid Chromatography", Analytical Biochemistry 211 :279-87 (1993).
Communication of a notice of opposition for EP Patent No. 2761296 mailed Jun. 5, 2018.
Communication pursuant to Article 94(3) EPC for Application No. EP17188121.2, dated Sep. 14, 2020, 3 pages.
Communication pursuant to Article 94(3) EPC issued in European U.S. Appl. No. 17/815,987 dated Dec. 7, 2020. (5 pges).
Communication pursuant to Article 94(3) EPC, dated Apr. 17, 2019, for Application No. EP15855907.0, 4 pages.
Communication pursuant to Article 94(3) EPC, for Application No. EP17820918.5, dated Nov. 26, 2020, 5 pages.
Cook et al., Development and Qualification of An Antibody Rapid Deglycosylation Method, Biologicals 2012; 40 (2): 109-17.
Cooper, D., et al., "LC-MS-MS Analysis of Amino Acids Using AccQ-Tag derivatisation, Application Brief AB25", Micromass June and Sep. 2000.
Cooper, D., et al., "LC-MS/MS Analysis of AccQ-Tag Derivatised Amino Acids", Micromass UK Limited pp. 1-7 (2000).
Cooper, D., et al., LC-MS/MS Analysis of AccQ-Tag Derivatised Amino Acids, Micromass Application Brief, Sep. 2000 and Jun. 2000.
Cosgrave, E and McCarthy,. M Investigation of the Factors that Contribute to Glycan Separation in HI LIC, Business Operations, Pharmaceutical Life Sciences, Waters Corporation (Year: 2014).
De Antonis, K. M., et al., "High-Performance Liquid Chromatographic Analysis of Synthetic Peptides Using Derivatization with 6-Aminoquinolyl-N-Hydroxysuccinimidyl Carbamate", Analytical Biochemistry 223:191-197 (1994).
de Hoffmann, "Tandem Mass Spectrometry: a Primer," J. Mass Spec. 1996, 31, 129-137. Abstract.
Decision on Rejection, Chinese Application No. 201280047599.3, dated Dec. 5, 2016, Original and translated.
Dell, "Fast Atom Bombardment Mass Spectrometric Strategies for Characterizing Carbohydratec-Containing Biopolymers," Biomedical and Environmental Mass Spectrometry, 1998, 16, 19-24. Abstract.
Dextran Calibration Ladder Standard. Waters (2012), 3 pages.
Dextran Calibration Ladder. Waters. Product Solution (2013) 3 pages.
EP Communication pursuant to Article 94(3) EPC, EP Application No. 12836127.6, dated Sep. 26, 2016.
EP Communication under Rule 71(3) EPC, EP Application No. 12836127.6, dated Mar. 15, 2017.
EP Communication with extended search report, EP Application No. 15180680.9, dated Feb. 2, 2016.
EP12836127.6 Opposition Communication Jul. 23, 2019, 25 pages.

European Search Report and Written Opinion dated Aug. 26, 2014 regarding patent application No. EP 12836127.6, 5 pages.
European Search Report and Written Opinion dated Feb. 2, 2016 regarding patent application No. EP 15180680.9, 7 pages.
Rudd, "Rapid, sensitive sequencing of oligosaccharides from glycoproteins," Current Opinion in Biotechnology 1997, g:488-497.
Ruhaak et al. Glycan Labeling Strategies and their use in Identification and Qualification, Anal Bioanal Chem 2010, 397 (8), 3457-81.
Saurina, J., et al., "Chromatographic Determination of Amino Acids by Pre-col. Derivatization Using 1,2-Napthoquinone-4-Sulfonate As Reagent", Journal of Chromatography A, 740:21-30 (1996).
Saurina, J., et al., "Determination of Amino Acids by Ion-Pair Liquid Chromatography With Post-col. Derivatization Using 1,2-Naphlhoquinone-4-Sulfonale", Journal of Chromatography A,676:311-319 (1994).
Schmeer, K., et al., "Compositional Analysis of the Phenylthiocarbamyl Amino Acids by Liquid Chromatography-Atmospheric Pressure Ionization Mass Spectrometry with Particular Attention to the Cyst(e)ine Derivatives", Journal of Chromatography A, 691:285-299 (1995).
Schmidt, C.J., et al., "Amino Acid Profiling of Protein Hydrolysates Using Liquid Chromatography and Fluorescence Detection", Journal of Liquid Chromatography 2(7):1031-1045 (1979).
Schwartz, "Multistage mass spectrometry: Scan modes and new instrumentation" Dissertation 1989.
Schwartz, "Systematic Delineation of Scan Modes in Multidimensional Mass Spectrometry," Anal. Chem. 1990, 52:1809-1818. Abstract.
Schwartz, B., et al., "A Kinetic Characterization of the Glycosyltransferase Activity of *Eschericia coli* PBP1b and Development of a Continuous Fluorescence Assay", Biochemistry, 41: 12552-12561 (2002).
Search Report for GB1509402.2 mailed Mar. 1, 2016.
Shimbo, "Multifunctional and Highly Sensitive Precolumn Reagents for Amino Acids in Liquid Chromatography/Tandem Mass Spectrometry," Anal. Chem. 2009, 81, 5172-5179. Abstract.
Snyder, "Introduction to Modern Liquid Chromatography," Second Edition, John Wiley & Sons, nc. 1979, Introduction, Chapters 2, 4, 13, 14, 17. Abstract.
Song, X., et al., "Glycan microarrays offfluorescently-tagged natural glycans", Glycoconjugate Journal, 32:465-473 (2015).
Spengler, "Peptide sequencing of charged derivatives by postsource decay MALDI mass spectrometry," Inl. J. Mass Spectrom. Ion Processes 1997, 169/170, 127-140.
Statement of grounds appeal for European patent application No. 15180680.9, dated May 20, 2020, 4 pages.
Stockmann, Ultrahigh Throughput, Ultrafiltration-Based N-Glycomics Platform for Ultraperformance Liquid Chromatography (ULTRA3) Anal. Chem. 2015, 87, 8316-8322. Abstract.
Struwe et al. 'Aminoquinolines as fluorescent labels for hydrophilic interaction liquid chromatography of Iligosaccharides', Biological Chemistry, 2012, vol. 393, pp. 757-765.
Summons to attend oral proceedings pursuant to Rule 115(1) EPC for Application No. EP15180680.9, dated Jul. 18, 2019, 4 pages.
Summons to attend oral proceedings pursuant to Rule 115(1) EPC for Application No. EP15180680.9, dated Jun. 17, 2019, 9 pages.
Supplementary European Search Report, EP12836127.6 dated Sep. 12, 2014 and Response dated Mar. 19, 2015.
Suzuki.et al, "Comparision of the Sensitivities of Various Derivatives of Oligosacchardies in LC/MS with Fast Atom Bombardment and Electrospray Ionization Interfaces", Analytical Chemistry 68(13):2073-2083 (1996).
Synder, "Practical HPLC Method Development," Second Edition, John Wiley & Sons, Inc. 1997, Chapters 3, 4. Abstract.
Takeda, K., et al., Convenient Methods for Syntheses of Active Carbamates, Ureas and Nitrosoureas Using N,N'-Disuccinimido Carbonate (DSC), Tetrahedron Letters 24(42):4569-72 (1983).
Tarentino et al., 2-Iminothiolane: A Reagent for the Introduction of Sulphydryl Groups into Oligosaccharides Derived from Asparagine-linked Glycans, Glycobiology 1993; 3 (3): 279-85.
Tousi "The Pursuit of Cancer Biomarkers: Liquid Chromatography and Mass Spectrometry 1-13 Platforms for Glycomic Characterization of Biospecimens" Northeastern University, Jul. 16, 2013.

(56) References Cited

OTHER PUBLICATIONS

Ullmer et al. "Derivatization by 6-aminoquinolyl-N-hydroxysuccinimidyl carbamate for enhancing the ionization yield of small peptides and glycopeptides in matrix-assisted laser desoprtion/ionization and electrospray ionization mass spectrometry", Rapid Communications in Mass Spectrometry, 20:1469-1479 (2006).
Van Wandelen, C., et al., "Using Quaternary High-Performance Liquid Chromatography Eluenl Systems for Separating 6-Aminoquinolyl-N-Hydroxysuccinimidyl Carbamale-Derivatized Amino Acid Mixtures", Journal of Chromatography A, 763:11-22 (1997).
Vasilevich, N., et al., "Conversion of O-Succinimidyl Carbamales to N-(O-Carbamoyl)-Succinmonoamides and Ureas: Effects of N-Subslituenls and Reaction Conditions on the Reaction Pathway", Tetrahedron Letters 43:6649-6652 2002) Abstract.
Voet, "Biochemistry" Second Edition, John Wiley & Sons, Inc. 1995, Chapters 4, 5. Abstract.
Vollhardt, "Organic Chemistry Structure and Function," Third Edition, W. H. Freeman and Company, 1999, Chapters 14, 20, 21, 26. Abstract.
Wada, Y., et al., "Comparison of the Methods For Profiling Glycoprotein Glycans—HUPO Human Disease Glycomics/Proteome Initiative Multi-Institutional Study", Glycobiology 17(4):411-422 (2007).
Walker et al. "Hydrophobic Derivatization of N-linked Glycans for Increased Ion Abundance in Electrospray Ionization Mass Spectrometry." J. Am. Soc. Mass. Spectrom. 22.8(2011): 1309-1317.
Waters Corporation "GlycoWorks High-Throughput Sample Preparation Kit" (Sep. 2013).
Wei, W-J., et al., "Study on N-Hydroxyphlhalimide as Blocking Agent for Isocyanales", Journal of Applied Polymer Science 84:1346-1352 (2002).
West, C., et al., "Porous Graphitic Carbon: a Versatile Stationary Phase for Liquid Chromatography", J Chromatogr A 1217(19):3201-16 (2010).
Wuhrer, M., et al., "Nano-Scale Liquid Chromatography-Mass Spectrometry of 2-Aminobenzamide-Labeled Oligosaccharides at Low Femtomole Sensitivity", International Journal of Mass Spectrometry 232:51-57 (2004).
Yang et al. "Solid-phase glycan isolation for glycomics analysis." Prote. Clin. Appl. 6.0(2012): 596-608.
Yodoshi et al. "Optimized conditions for high-performance liquid chromatography analysis of oligosaccharides using 7-amino-4-methylcoumarin as a reductive amination reagent." J. Chromatogr. A. 1203.2(2008): 137-145.
Yu et al., "A Rapid Sample Preparation Method for Mass Spectrometric Characterization of N-linked Glycans", Rapid Communications in Mass Spectrometry, 19:2331-2336 (2005).
Yu et al., A Rapid Sample Preparation Method for Mass Spectrometric Characterization of N-linked Glycans, Rapid Commun. Mass Spectrom 2005; 19: 2331-6.
Yu Y. Q., "N-linked Glycan Characterization and Profiling: Combining the Power of Accurate Mass, Reference Glucose Units, and UNIFI Software for Confident Glycan Assignments, " Waters, Application Note (2013) 10 pages.
Zailin, W., "Studies on Fluorescent Labeling of Several Fungal Polysaccharides", Chinese Master's Thesis, Agriculture Science and Technology, No. 5 (2013).
Zhang ed., Biological Sample Library Establishment and Practice, p. 102 Sun Yat-Sen University Press (Oct. 2013).
Zhang Li et al., "Practical Guidance of Detection by Separation", Press of University of Science and Technology of China, Jan. 2013, p. 55.

\* cited by examiner

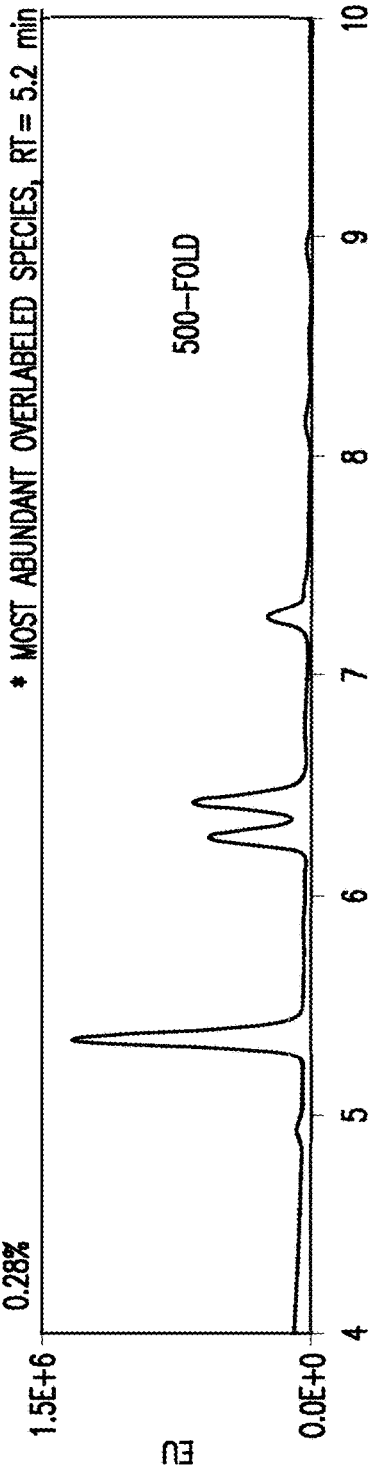
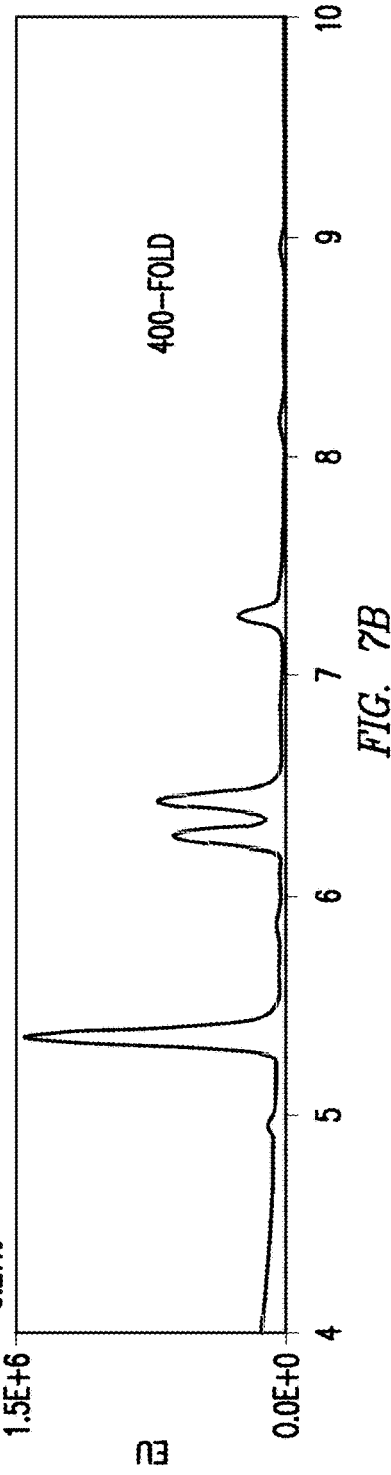

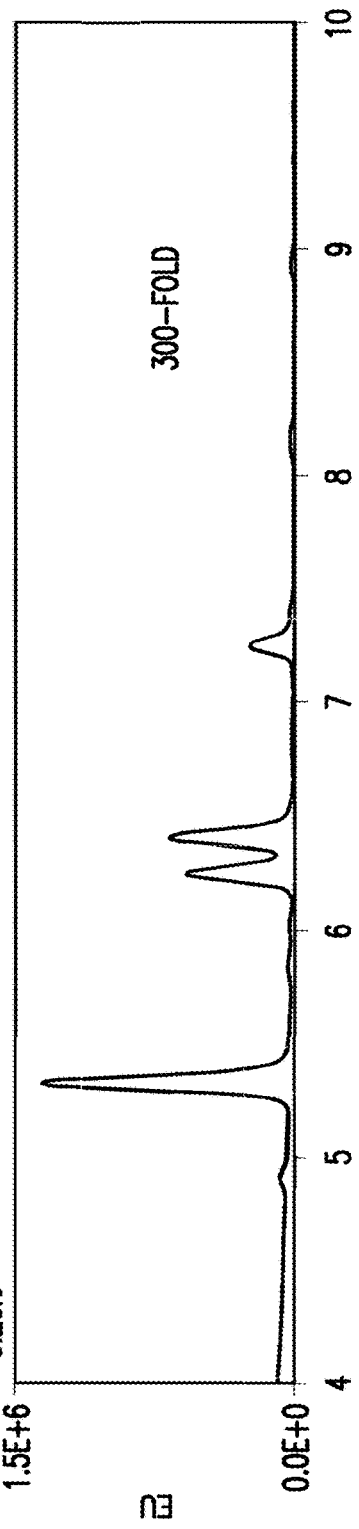
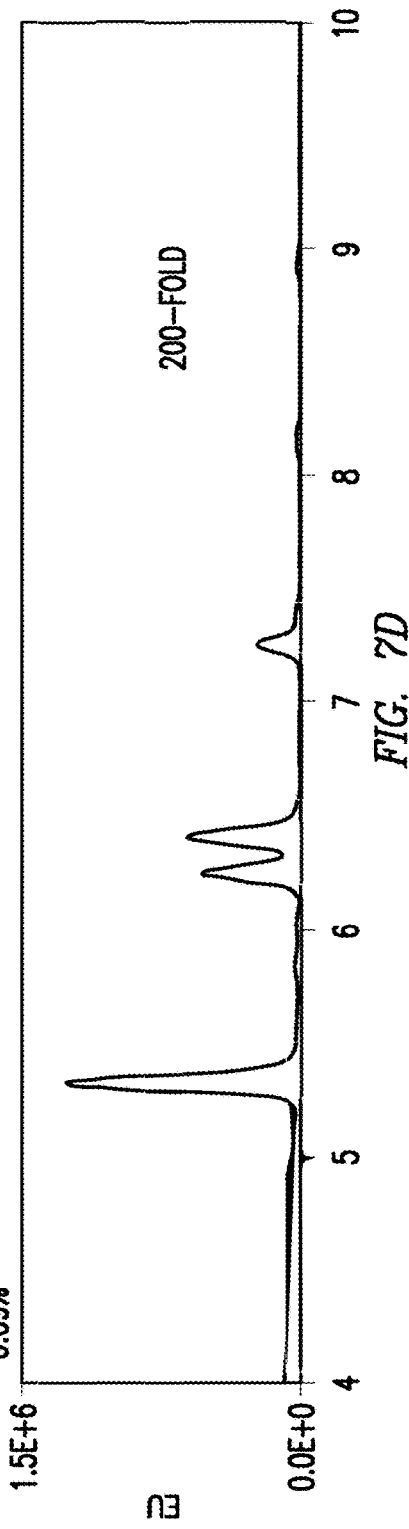

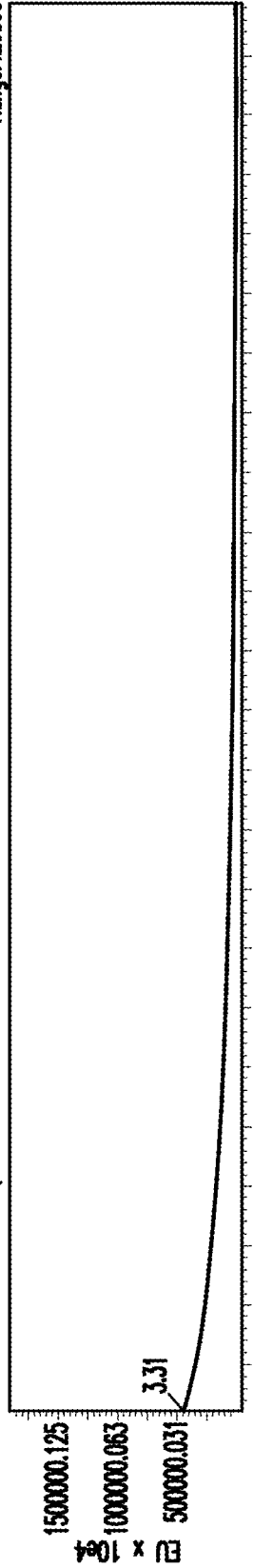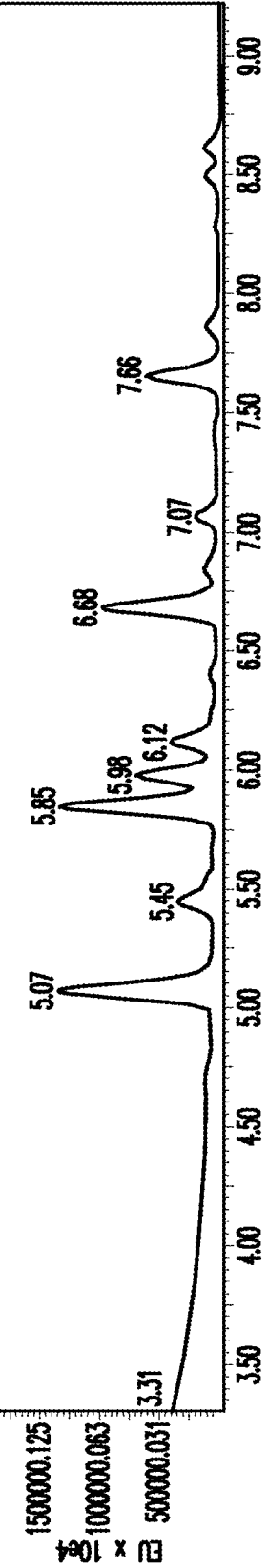
FIG. 9A
FIG. 9B

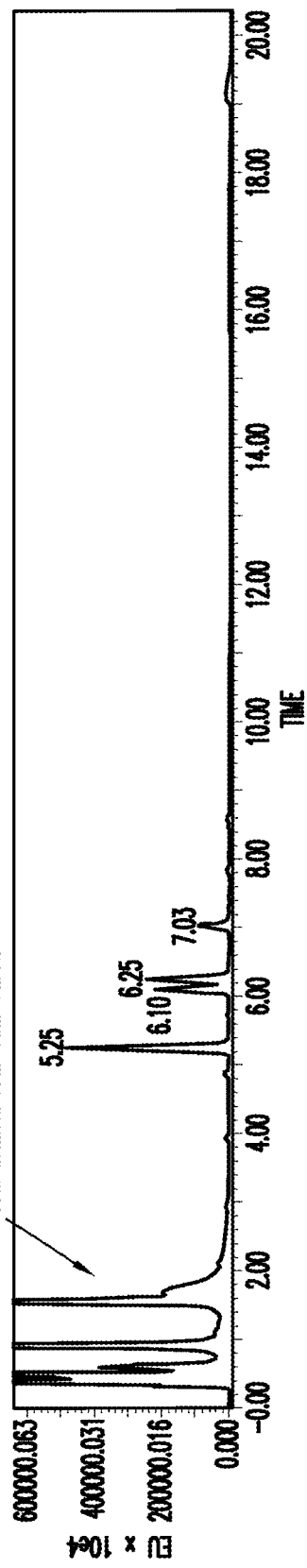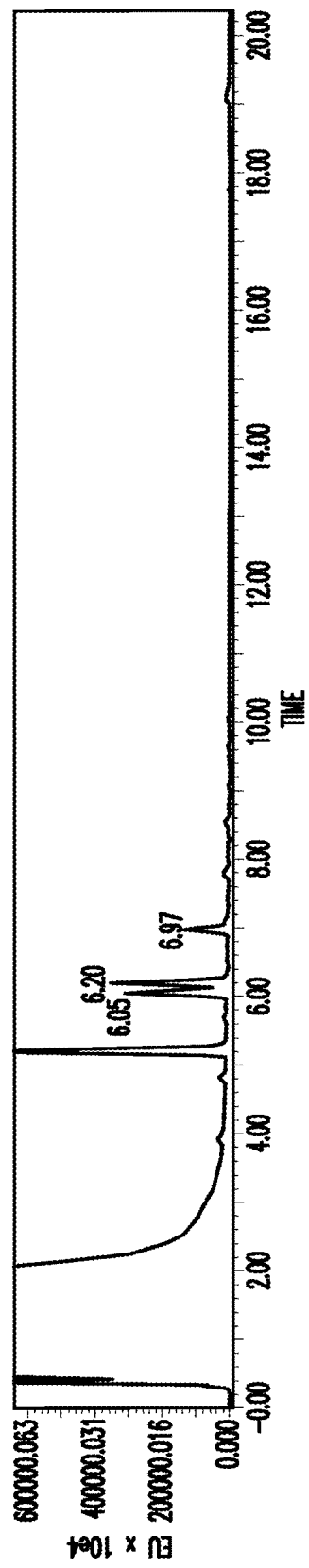
FIG. 12A
FIG. 12B

METHODS FOR THE RAPID PREPARATION OF LABELED GLYCOSYLAMINES AND FOR THE ANALYSIS OF GLYCOSYLATED BIOMOLECULES PRODUCING THE SAME

CROSS REFERENCE TO RELATED APPLICATIONS

This application is a continuation of U.S. application Ser. No. 15/522,908 filed Apr. 28, 2017, which is a 371 National Stage filing of International Application No. PCT/US2015/057848 filed Oct. 28, 2015 which claims priority to U.S. Provisional Patent Application No. 62/107,994 filed Jan. 26, 2015 and U.S. Provisional Patent Application No. 62/072,747 filed Oct. 30, 2014. The contents of each are incorporated herein by reference in their entirety.

STATEMENT REGARDING FEDERALLY SPONSORED RESEARCH OR DEVELOPMENT

None.

THE NAMES OF PARTIES TO A JOINT RESEARCH AGREEMENT

None.

BACKGROUND

Methods of analyzing compounds from biological sources often include a derivatization step to introduce a fluorophore that facilitates detection after chromatographic separation. While different derivatization strategies exist, long processing times are a serious factor in effectively employing the analytical data once obtained. Reagents and associated methods have been recently developed to reduce the lead time, particularly with regard to analysis of compounds having an amine or amino group. Yet desired reaction selectivity between primary amines and hydroxyl groups is not often achieved. In turn, the yield of labeled compounds is not optimized. In addition, prior art methods frequently generate "over-labeled" compounds. Moreover, the solubility of a labeled or tagged compound in high organic solvents can be low, hindering downstream solid-phase extraction procedures ("SPE"), especially those based on hydrophilic interaction chromatography. Also, prior art analysis typically requires that the compound be separated from the biological source and/or undergo a wash step prior to derivatization, generating additional steps and slowing down the analytical procedure.

Therefore, a need exists for methods of analyzing compounds where the derivatization step produces tagged compounds in a high yield which are selectively labeled, and without causing degradation of the biological sample or over-labeling to provide high resolution during subsequent analysis of the labeled compounds.

SUMMARY OF INVENTION

A method of analyzing glycosylated biomolecules comprising the steps of: (a) producing a deglycosylation mixture, wherein the glycosylated biomolecules have been deglycosylated by natural or synthetic enzymatic or chemical techniques; (b) providing a reagent solution comprising a labeling reagent in a polar aprotic, non-nucleophilic organic solvent; (c) mixing the deglycosylation mixture with the reagent solution in a volumetric ratio of about 2.5 to about 1 in a reaction mixture; and (d) detecting the derivatized glycosylamines. The reaction mixture contains a molar excess of labeling reagent over modifiable amine in an amount ranging from: about 10 to about 2000 and can include the released glycosylamines, proteinaceous amines and derivatized glycosylamines. The steps can be carried out purposefully without depletion of protein matter. The derivatized glycosylamines can be then separated from the reaction mixture with online or offline SPE and/or other separation methods, or not separated from the reaction mixture. Optionally, a quenching solution can be added to the reaction mixture so that the pH of the reaction mixture is shifted to above 10. The yield of derivatized glycosylamines can be in an amount of about 80 to about 100 mole percent of the reaction mixture. The derivizated glycosylamines are then separated from the reaction mixture and detected by chromatographic detection, fluorescence detection, mass spectrometry ("MS"), or Ultra Violet ("UV") detection and/or a combination thereof. In some embodiments, the methods may further include the step of contacting the glycosylated biomolecules with an enzyme to produce a deglycosylation mixture or can be deglycosylated through other enzymatic or chemical techniques.

In another aspect, methods of rapid derivatization of glycosylamines are also described herein. In some embodiments, the methods of rapid derivatization of glycosylamines include the steps of: (1) providing a biological sample; (2) combining the biological sample with peptide N-glycosidase F to produce a deglycosylation mixture; (3) providing a reagent solution comprising a labeling reagent combined in anhydrous dimethylformamide (DMF); and (4) mixing the deglycosylation mixture with the reagent solution to produce a reaction mixture comprising the labeling reagent, released glycosylamines, proteinaceous amines and derivatized glycosylamines. The reaction mixture can have a molar excess of labeling reagent over modifiable amine in an amount of about 10 to about 1000. For some embodiments, other ranges of molar excess are also described herein.

In the described methods, the concentration of organic solvent in the reaction mixture can be about 0 to about 50 percent. In some embodiments, the range of organic solvent in the reaction mixture can be about 10 to about 40 percent. In some exemplary embodiments, the range of organic solvent in the reaction mixture can be about 20 percent to about 30 percent by volume. The deglycosylation mixture is mixed with the reagent solution in a volumetric ratio of about 9:1 to about 1:9. In exemplary embodiments, the deglycosylation mixture is mixed with the reagent solution in a volumetric ratio of about 2.5 to about 1 to produce a reaction mixture having about 25 to about 30 percent reagent solution. In some embodiments, the amount of reagent solution in the reaction mixture is 28.6 percent. The reagent solution can be at a temperature maintained at about ambient temperature or less than ambient temperature to about 4° C. A buffer solution can be added to the deglycosylation mixture. The buffer solution can be sodium phosphate or HEPES. Alternatively, the biological sample can be deglycosylated in a buffer solution, such as HEPES, so as to facilitate subsequent derivatization reactions with fewer steps.

Optionally, a quenching solution can be added to the reaction mixture. The quenching solution can comprise ethylene diamine. The ratio of ethylene diamine to water to acetonitrile can be about 5 to about 5 to about 90 by volume. The quenching solution then can be added to the reaction mixture at about 2 to about 10 minutes after the deglycosylation mixture is mixed with the reagent solution. The pH of the reaction mixture can shift to about greater than 10.

Generally, to prepare the glycosylated biomolecule for analysis, it can be deglycosylated either synthetically or naturally. More specifically, to prepare labeled N-glycans, biological samples can have glycosylated biomolecules such as glycoproteins which can be deglycosylated with peptide N-glycosidase F (PNGase F) producing the deglycosylation mixture. A labeling reagent can be combined in anhydrous dimethylformamide (DMF) and/or other polar aprotic non-nucleophilic organic solvent to produce the reagent solution. The deglycosylation mixture and the reagent solution are subsequently mixed in an about 2.5 to about 1 volumetric ratio (2.5:1 v/v/v) to produce a reaction mixture and the glycosylamine can be rapidly labeled with the labeling reagent. The derivatized glycosylamine can be subjected to chromatographic analysis, mass spectrometry, ultraviolet and/or fluorescence detection.

The methods for the rapid labeling of glycosylamines described herein can include alternative types of separation and detection methods. The separation techniques can include, but are not limited to, hydrophilic interaction chromatography ("HILIC"), solid phase extraction ("SPE"), capillary electrophoresis, high pH anion exchange chromatography, or reversed phase liquid chromatography. Detection methods can include chromatographic detection such as high pressure liquid chromatography ("HPLC"), ultra high performance liquid chromatography (UHPLC), supercritical fluid chromatography, ultra violet ("UV") detection, fluorescence detection, matrix assisted laser desorption ionization mass spectrometry, electrospray ionization mass spectrometry, and/or pulsed amperometric detection.

BRIEF DESCRIPTION OF THE DRAWINGS

FIG. 5A shows the effect of buffer concentration and ionic strength on the yield of amino-labeled groups of Bradykinin. FIG. 5B shows the effect of buffer concentration and ionic strength on the yield of hydroxyl groups of Bradykinin.

FIGS. 7A, 7B, 7C, 7D and 7E are chromatograms showing the effect of molar excess of tagging reagent on the yield of amino-labeled groups and on the levels of over-labeled glycans. These figures demonstrate how the molar excess of reagent to glycosylamines must be optimized in order to achieve high yields (greater than 80 percent) without introduction of high (greater than 0.2 mole percent) levels of "over-labeled" species.

FIG. 8A shows the results after quenching with the addition of ethylene diamine post-reaction and after washing with 1:14:85 formic acid/water/ACN wash. FIG. 8B shows the results after quenching with the addition of isopropylamine post-reaction and after washing with 1:14:85 formic acid/water/ACN wash. FIG. 8C shows the results after quenching with the addition of hexylamine post-reaction and after washing with 1:14:85 formic acid/water/ACN wash.

FIGS. 9A, 9B and 9C are fluorescence chromatograms obtained for labeled glycosylamines showing different washes employed during SPE has different effects. FIG. 9A shows the chromatogram after washing with a ratio of about 15 to about 85 by volume (15:85 (v/v)) of DMF/ACN. FIG. 9B shows the chromatogram after washing with about 85 percent ACN. FIG. 9C shows the chromatogram after washing with a ratio of about 1 to about 14 to about 85 by volume (1:14:85 (v/v/v)) of formic acid/water/ACN.

FIG. 12A is a HILIC fluorescence chromatogram obtained for anti-citrinin murine IgG1 glycosylamines labeled with Labeling Reagent-1 resulting from SPE of HEPES buffered reactions.

FIG. 12B is a HILIC fluorescence chromatogram obtained for anti-citrinin murine IgG1 glycosylamines labeled with Labeling Reagent-1 resulting from SPE of phosphate buffered reactions.

DETAILED DESCRIPTION OF THE INVENTION

Figure 1:
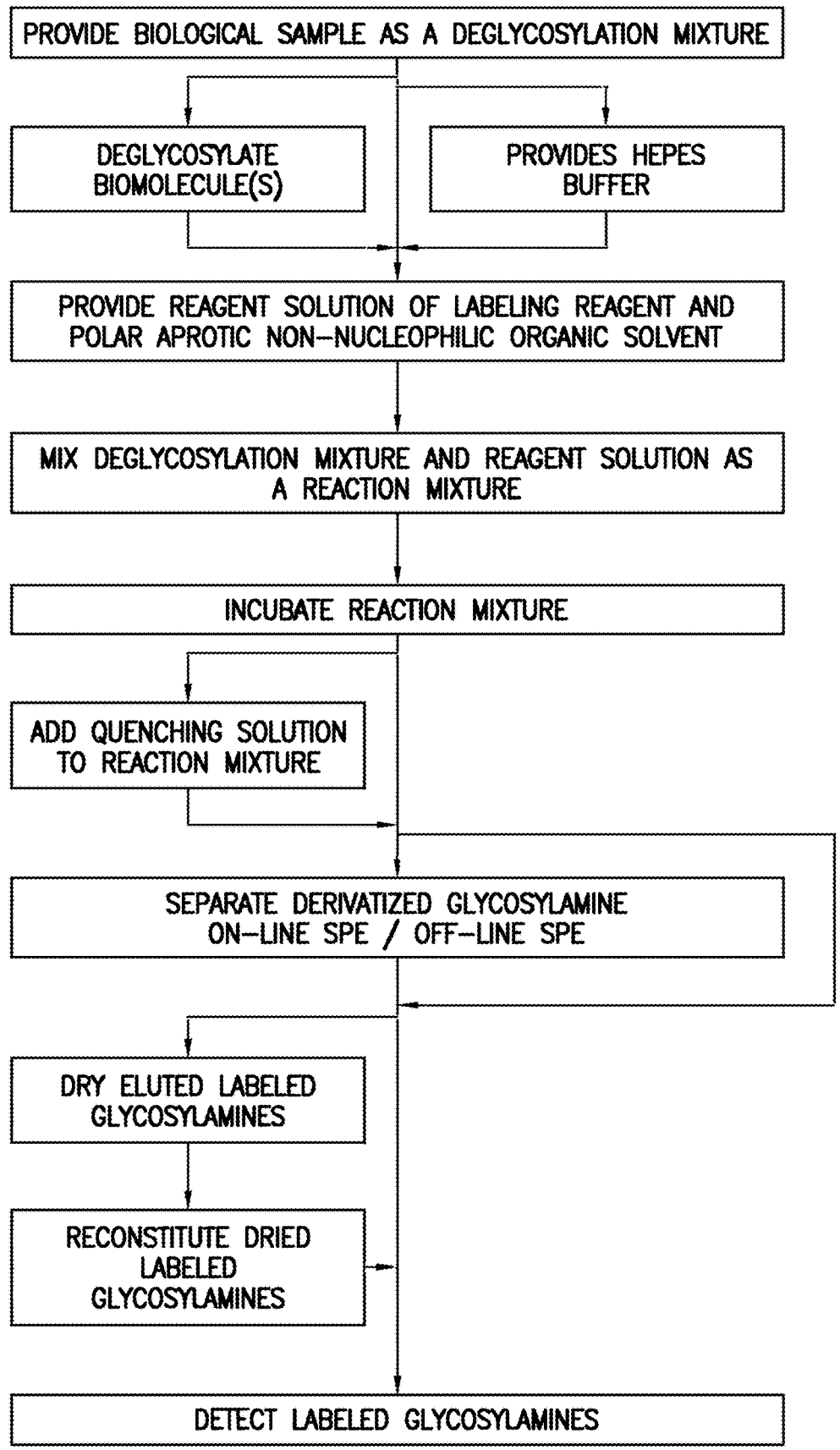
FIG. 1 is a flow diagram showing steps of the methods described herein.

Novel methods of analyzing compounds of biological samples are provided herein. To analyze the glycosylated biomolecule, the molecule is deglycosylated naturally or by synthetic processing, and then contacts a labeling reagent under select conditions to produce derivatized glycosylamines in optimized yields and with minimal over-labeling. Without first separating the biomolecules of the sample, derivatization is performed. Chromatographic analysis can also be performed directly on the obtained derivatization mixture and such analysis includes, but is not limited to, high pressure liquid chromatography ("HPLC"), ultra high performance liquid chromatography (UHPLC), mass spectrometry, supercritical fluid chromatography, ultraviolet ("UV") and/or fluorescent ("FLR") detection. Separation, however, is optionally including as described herein SPE offline and SPE online techniques.

The methods described herein are suitable for use in automated analysis and processing systems such as those described by Hewitson et al., U.S. Patent Application No. 62/100,252, incorporated herein by reference. These automated sampling and reaction systems for high pressure liquid chromatography or detectors for a wide variety of applications including, but not limited to, protein and peptide identification and quantitation, monitoring and analysis of cell culture media and nutritional content of food and feed are provided herein. The automated sampling and reaction systems can deliver turn-key analysis that can be optimized for high pressure liquid chromatography process and detection. The disclosed methods and systems can be used with different types of detectors, TUV, PDA or FLR detectors. The automated sampling and reaction systems are also useful for application-specific performance qualification, providing the same result: day-to-day, instrument-to-instrument, lab-to-lab around the world.

In addition, the methods described herein are appropriate for use in various production and distribution automated workflow systems and solutions. The methods described herein can be used in automated workflow systems for liquid handling and those using robotics, to increase throughput and bring improved efficiency and safety to the laboratory. Automated workflow systems often serve as platforms for biopharma, research and clinical diagnosis and include, but are not limited to, digital dispensers, DNA extraction, PCR setup, Elisa, multichannel pipetting, pipetting platforms, and related instrumentation and software that is integrated to make high performance workflow in the laboratory.

In the present methods, glycosylamines are labeled in-solution under conditions in which protein matter has not been depleted from the mixture. Conditions of the reaction mixture, including temperature, organic solvent composition, organic solvent concentration, buffer composition, pH, ionic strength, molar excess of reagent, and time are selected and controlled so that the desired reaction selectivity between the primary amines and hydroxyl groups of the glycosylamines can be achieved. In the methods described herein, conditions for the labeling or tagging the glycosylamines with various labeling reagents, particularly rapid tagging labeling reagents, are optimal.

As used herein, the phrase "a glycosylated biomolecule" means and includes proteins, peptides, glycans, amino acids, lipids, DNA, RNA and nucleic acid. The glycosylated biomolecule (sometimes referred to also as a biomolecule or compound, in the singular or in the plural) to be analyzed may natively have or can produce a glycan with a primary amine, a secondary amine, or a tertiary amine. The primary amine and secondary amine may be present singularly or in plural. Primary and secondary amines are considered "modifiable" amines for labeling reagents described herein. More specifically, an amine is an organic compound with functional groups that contain a nitrogen atom with a lone pair of electrons. Generally, amines are derivatives of ammonia, wherein one or more hydrogen atoms have been replaced by a substituent such as an alkyl or aryl group. Exemplary amines include an amino acid, biogenic amine, trimethylamine, and aniline. Inorganic derivatives of ammonia are also referred to herein as amines. Additionally, glycosylated biomolecules may be of a single type or of a mixture of plural kinds within a sample. The glycosylated biomolecule can include, but are not limited to, amines (primary, secondary, and the like), amino acid, peptide, protein, polyamine, a glycosylated compound, compound with glycan group or glycoprotein and the like.

More generally, the glycosylated biomolecule can mean any molecule to which a sugar has been added either naturally or by synthetic processing. Hence, a glycosylated biomolecule, glycosylated compound or glycoprotein is a compound or molecule that has undergone co-translational or post-translational modification and contains one or more carbohydrates attached thereto and a glycan group. Such glycosylated compounds may be naturally occurring or synthetically produced and include proteins, lipids, amino acids (even when occurring as residues in peptides and proteins), antibodies, peptides, or other organic molecules. N-glycans (or N-linked glycans) can attach to a nitrogen of an amide or amine group of asparagine or arginine side-chains. On the other hand, O-linked glycans can be attached to the hydroxyl oxygen of serine, threonine, tyrosine, hydroxylysine, or hydroxyproline side-chains, or to oxygens on lipids. In the context of the methods presented herein, the glycosylated compounds may be present in a sample singly or in a plural number.

Glycosylamines, or N-glycosides, are a class of compounds consisting of an amine with a β-N-glycosidic bond to a carbohydrate, forming a cyclic hemiaminal ether bond (α-aminoether). In other words, glycosylamines are compounds having a glycosyl group attached to an amino group. Glycosylamines can include, but are not limited to, nucleosides such as adenosine, and glycosides with an amine group such as N,N-dimethyl-β-D-glucopyranosylamine, glucosylamine, glucosyl-n-butylamine, glucosyl-n-hexylamine, glucosyl-n-octylamine, glucosyl-n-decylamine, glucosyl-n-dodecylamine, maltosyl-n-dodecylamine. Furthermore, D-glucose, D-galactose, lactose, cellobiose, and maltose will all yield corresponding glycosylamine, 1-amino-1-deoxy-D-glucose, 1-amino-1-deoxy-D-galactose, 1-amino-1-deoxylactose, 1-amino-1-deoxycellobiose and 1-amino-1-deoxymaltose, upon treatment with aqueous solution of ammonia in the presence of one equivalent of ammonium hydrogen carbonate.

Specific glycosylation patterns have been associated with states of health and disease and N-glycan analysis is increasingly applied by multiple industries, including pharmaceutical biotechnological production. Many protein-based biopharmaceuticals are glycosylated proteins and uncontrolled changes in protein glycosylation are of great regulatory concern. For example, relative amounts of the individual glycan structures need to be monitored during process development to establish the stability of the growth and purification steps of manufacturing. Fluorescent labeling of N-glycans (a form of glycosylamine) is beneficial to detecting the distribution profiles of N-glycans of amino acids in biological samples because it improves both sensitivity and selectivity of the detection as well as the chromatographic behavior of glycans.

As such, a wide variety of enzymatic and chemical techniques are available for protein deglycosylation and glycan release. The enzymatic deglycosylation techniques utilize glycosidases that can include, but are not limited to, N-glycosidase A (PNGase A), N-glycosidase F (PNGase F), O-glycosidase, Neuraminidase, β1-4 Galactosidase and β-N-Acetylglucosaminidase. For example, as described in detail herein, glycoprotein samples can be deglycosylated with the enzyme, peptide N-glycosidase F (PNGase F), which removes N-linked oligosaccharides from glycoproteins, except for compounds containing α(1-3)-linked fucose on the reducing terminal. N-glycosidase A (PNGase A) can remove all N-glycans, however. Other useful enzymes include endoglycosidases or glycoamidases such as endoglycosidase and N-glycanase. Upon enzymatic deglycosylation, N-glycans are released from asparagines residue as glycosylamines.

For a chemical release of N-glycans from the glycoproteins, the glycoproteins can be treated with anhydrous hydrazine at 90° C. for several hours. To release O-glycans from glycoproteins, glycoproteins are treated with O-glycanase or chemically treated with anhydrous hydrazine, specifically at 60° C. for up to 6 hours. Alternatively, O-glycans can be released by employing alkaline borohydrate for reductive alkali-catalyzed β-elimination, non-reductive β-elimination, or by using other releasing agents such as trifluoromethane-sulfuric acid or various amines. Other chemical techniques include, but are not limited to, hydrazynolysis and trifluoromethanesulfonic (TFMS) acid treatment.

Furthermore, glycan analysis is increasingly applied in biological research, and clinical analysis. Specific glycosylation patterns have been associated with states of health and disease. Moreover, glycosylation changes may modulate the biological activity of proteins as demonstrated for example, for the glycosylation of the Fc moiety of recombinant immunoglobulin. Hence, approaches for analysis of oligosaccharides from glycoproteins often focuses on the analysis of related and subsequently derivatized glycans. These approaches, however, allow in-depth analysis of the oligosaccharide structure independent of the carrier glycoprotein, but provide no information on the attachment site of the glycan.

Hence, characterization of the protein glycosylation profile is of great importance as it is required for various regulatory purposes and production of biopharmaceutical drugs. The released glycan pool is of vast complexity and structural heterogeneity, which requires an efficient method of separation and a highly sensitive detection method. Relative amounts of the individual glycan structures need to be monitored during process development to establish the stability of the growth and purification steps of manufacturing.

Hence, methods for the preparation of labeled glycosylamines are presented herein. Previously undescribed techniques are used together with a labeling reagent to rapidly produce analysis-ready glycans. These techniques include the labeling of glycosylamines with a labeling reagent comprised of a fluorescent moiety, a proton affinity/charge tag group(s), and an N-hydroxysuccinimide ester or carbamate reactive group such as identified below as Labeling Reagent-1, Labeling Reagent-2, Labeling Reagent-3, Labeling Reagent-4 in Table 1.

TABLE 1

| Labeling Reagent No. | Labeling Reagent Structure | Chemical Name | Other Reagent Reference Names |
|---|---|---|---|
| Labeling Reagent-1 | | 2,5-dioxopyrrolidin-1-yl (2-((2-(diethylamino)ethyl)carbamoyl) quinolin-6-yl)carbamate | RapiFluor-MS or RFMS |
| Labeling Reagent-2 | | 2,5-dioxopyrrolidin-1-yl (4-((2-(diethylamino)ethyl)carbamoyl) phenyl)carbamate | |
| Labeling Reagent-3 | | 2,5-dioxopyrrolidin-1-yl quinolin-6-ylcarbamate | |

TABLE 1-continued

| Labeling Reagent No. | Labeling Reagent Structure | Chemical Name | Other Reagent Reference Names |
|---|---|---|---|
| Labeling Reagent-4 | | 2,5-dioxopyrrolidin-1-yl methylcarbamate | |
| Labeling Reagent-5 | | 4-amino-N-(2-(diethylamino)ethyl)benzamide | Procainamide |
| Labeling Reagent-6 | | 2,5-dioxopyrrolidin-1-yl (4-carbamoylphenyl)carbamate | IAB, or Instant AB |
| Labeling Reagent-7 | | 2-aminobenzamide | 2-AB |

Other labeling reagents that can be used in connection with the methods described herein include those labeling reagents identified in U.S. patent application Ser. No. 14/458,760 entitled Rapid Fluorescence Tagging of Glycans and Other Biomolecules with Enhanced MS Signals, unpublished. See pages 2, lines 4 to page 4, line 9; page 11 line 4 to page 25, line 18 and page 29, line 1 to page 30 line 10 incorporated herein by reference. Additional labeling regents can also be found in U.S. Pat. No. 7,148,069 at Col. 8, 1. 56 to Col. 9, 1. 54 and Col. 15, 1. 22 to 29, incorporated herein by reference; U.S. Pat. No. 7,494,815 at Col. 7, 1. 19 to Col. 11, 1. 24, incorporated herein by reference; U.S. Pat. No. 8,124,792 at Col. 2, 1. 13 to Col. 4, 1. 5 and Col. 7, 1. 11 to Col. 17, 1. 20 incorporated herein by reference; and U.S. Pat. No. 5,296,599 at Col. 4, 1. 66 to Col. 5, 1. 32 and Col. 5, 1. 66 to Col. 7, 1. 28 incorporated herein by reference.

Moreover, the described methods can be the basis for the preparation of other labeled glycosylamines, including those derived from alternative labeling reagents. As described herein, such labeling reagents can have alternative reactive groups, such as isocyanates, isothiocyanates or imidates/thioimidates, and/or alternative functionalities such as a charge tag to enhance negative ion mode mass spectrometric analyses.

Conditions of the labeling reaction, including temperature, organic solvent composition, organic solvent concentration, buffer composition, pH, ionic strength, molar excess of reagent, and time are selected and controlled such that desired reaction selectivity between primary amines and hydroxyl groups is achieved. In turn, the yield of labeled glycans is optimized and the generation of so-called "over-labeled" glycans (glycans/glycosylamines modified by >1 label) is minimized. A quenching solution comprised of hydrophilic amine containing compound, ethylene diamine can also be used. This quenching solution not only controls the time a glycosylamine is allowed to react with the labeling reagent, but also shifts the pH of the reaction to an elevated pH (>10), which enhances the solubility of the labeled glycans in high organic solvents (i.e. >50% acetonitrile), and thereby facilitating downstream SPE procedures based on hydrophilic interaction chromatography ("HILIC").

Glycans released from glycoproteins are labeled in-solution under conditions in which protein matter has purposely not been depleted from the mixture. An exemplary labeling reaction is shown immediately below.

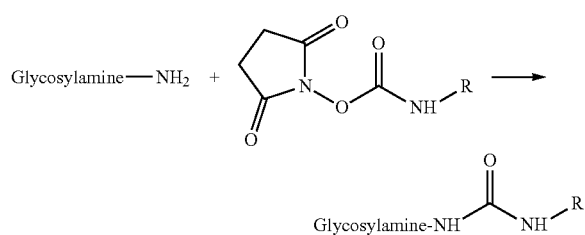

To develop and optimize the conditions for the methods of labeling of glycosylamines with a NHS carbamate reagent and/or a NHS ester reagent, N-succinimidyl N-methylcarbamate, a small, NHS carbamate reagent (Labeling Reagent-4) was reacted with a simple peptide, bradykinin. This peptide was used as a surrogate for glycosylamines, which cannot be easily studied in discrete experiments, given that they decompose to reducing sugars with aldehyde termini. Tarentino, A. L. et al., 2-*Iminothiolane: A Reagent for the Introduction of Sulphydryl Groups into Oligosaccharides Derived from Asparagine-linked Glycans*, Glycobiology 1993, 3 (3), 279-85. Bradykinin contains only one primary amine (its N-terminus) as well as one hydroxyl group and is, therefore, a useful tool in optimizing labeling yields and selectivity for glycosylamine derivatization. Bradykinin also contains two highly basic arginine residues, making it possible to assay reaction products by LC-MS, without concern over significant deviations in ionization efficiency when the N-terminus is labeled.

Figure 2:
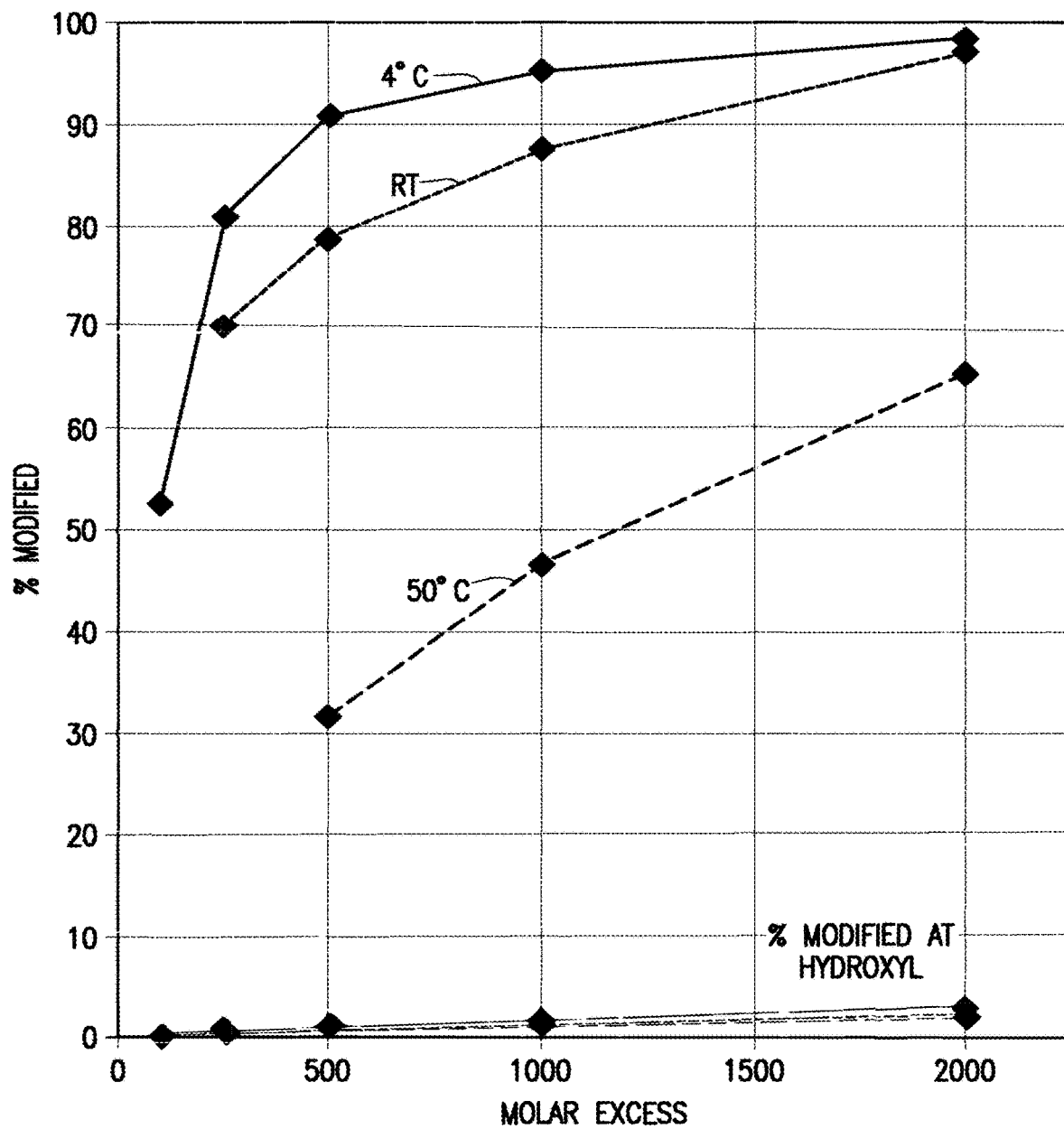
FIG. 2 is a chart showing the effect of temperature on the yield of amino-labeled groups and on the reaction selectivity between amine and hydroxyl groups of Bradykinin.
Figure 3A:
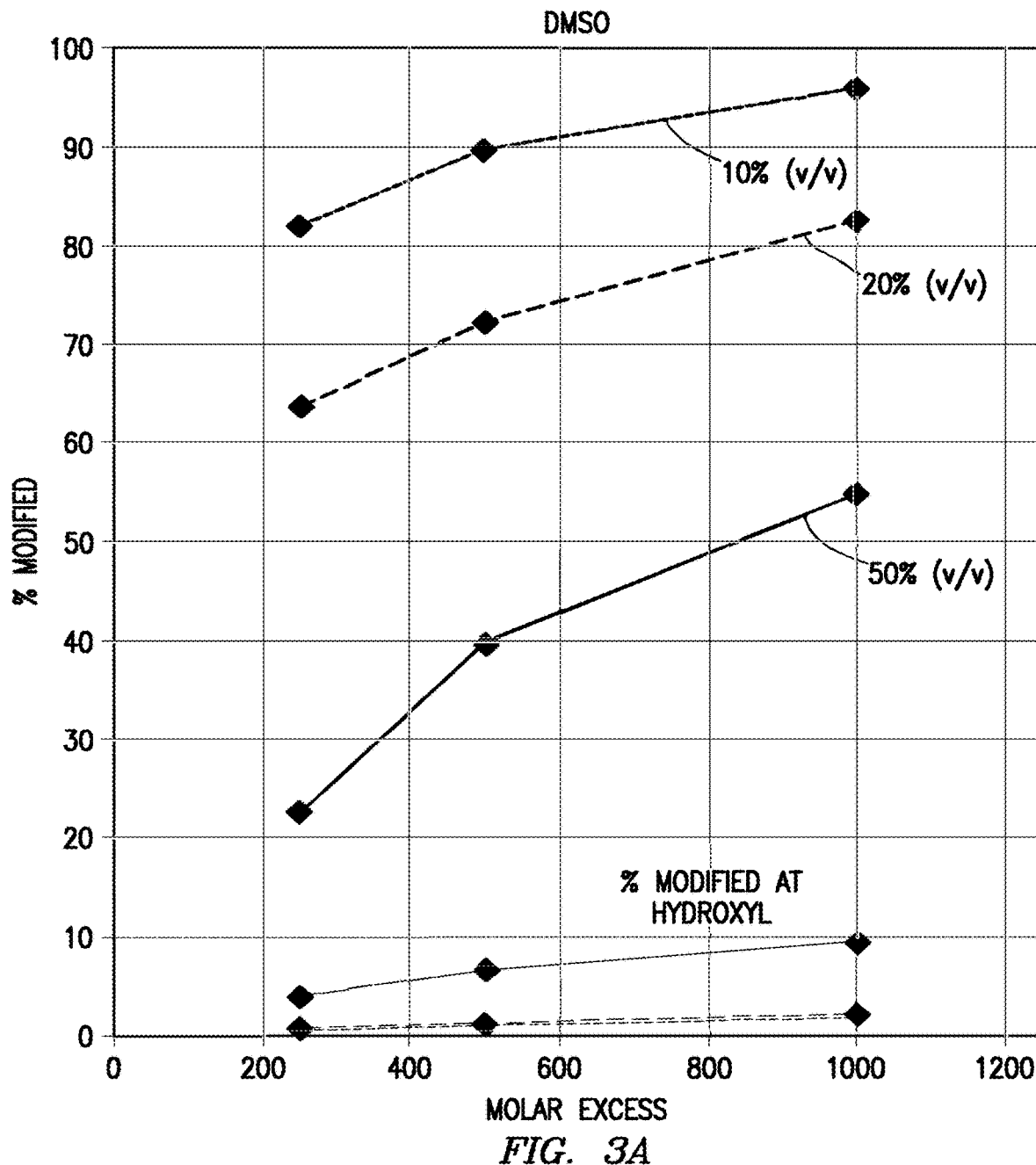
FIGS. 3A and 3B are each a graph that shows the effect of an organic solvent, DMSO and DMF, respectively, and organic solvent concentration on the yield of amino-labeled groups and on the reaction selectivity between amine and hydroxyl groups of Bradykinin.
Figure 3B:
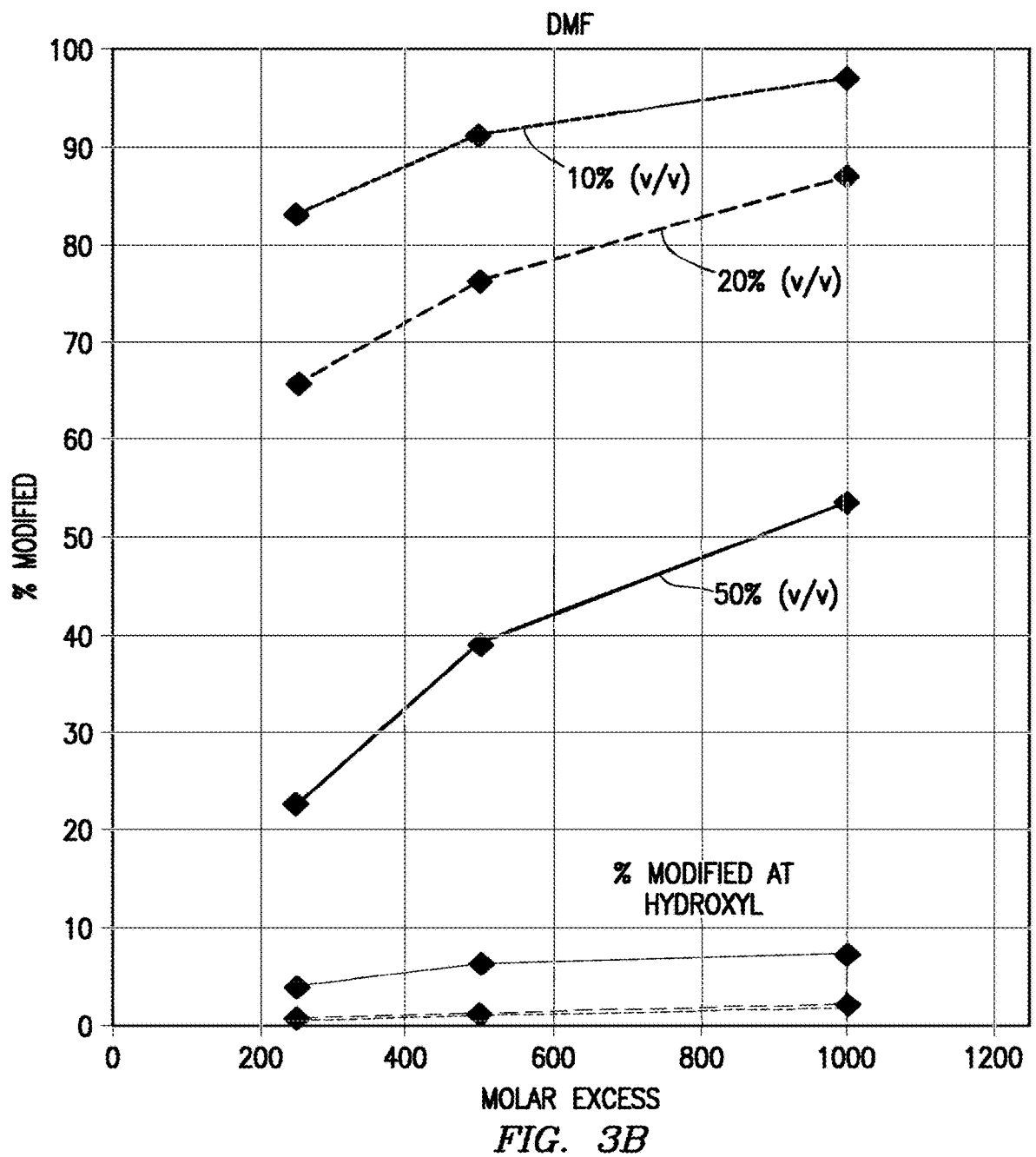
Figure 4A:
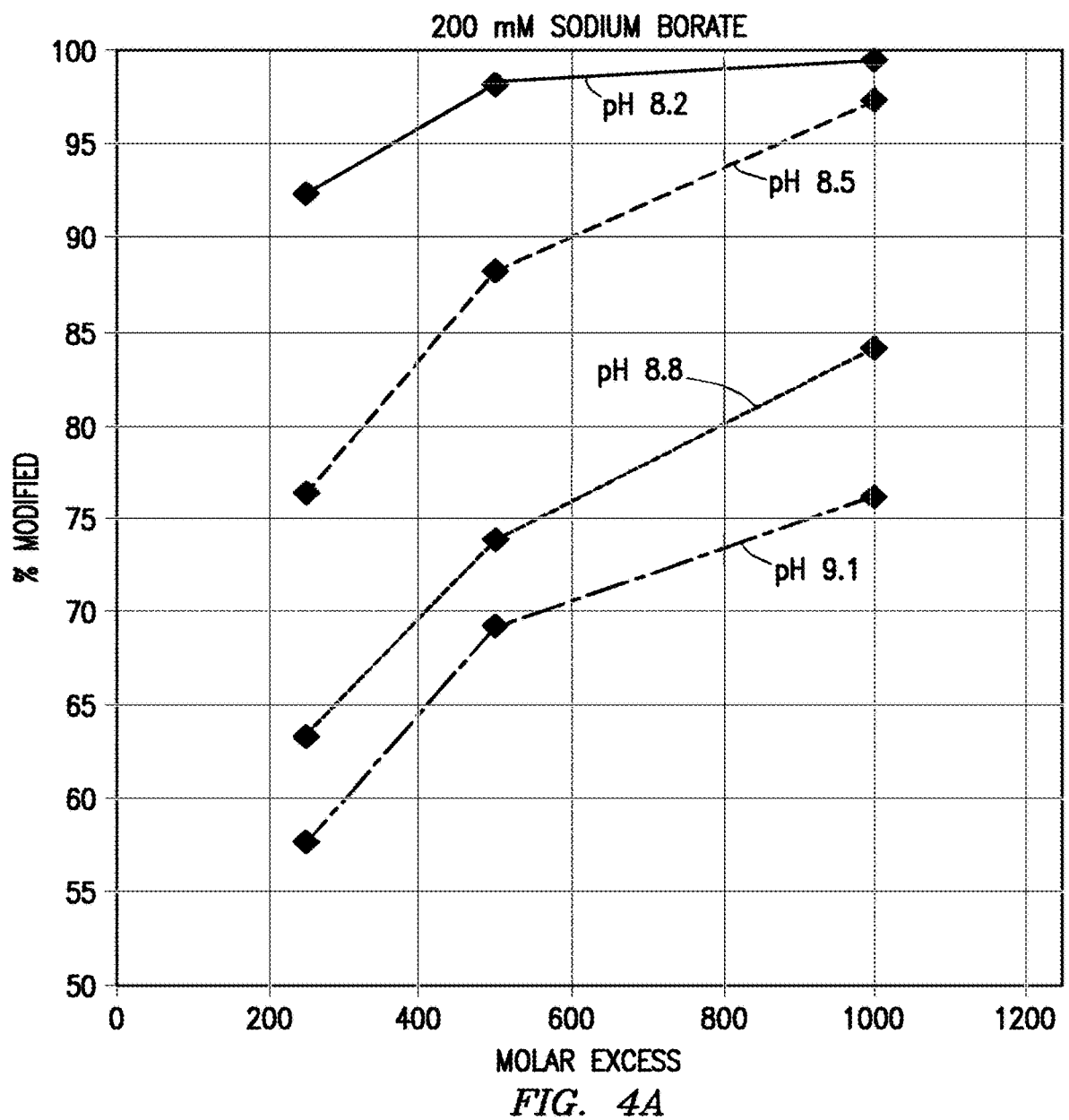
FIGS. 4A and 4B are graphs that show the effect of a buffer, 200 mM sodium borate, 200 mM sodium phosphate, respectively, on the yield of amino-labeled groups.
Figure 4B:
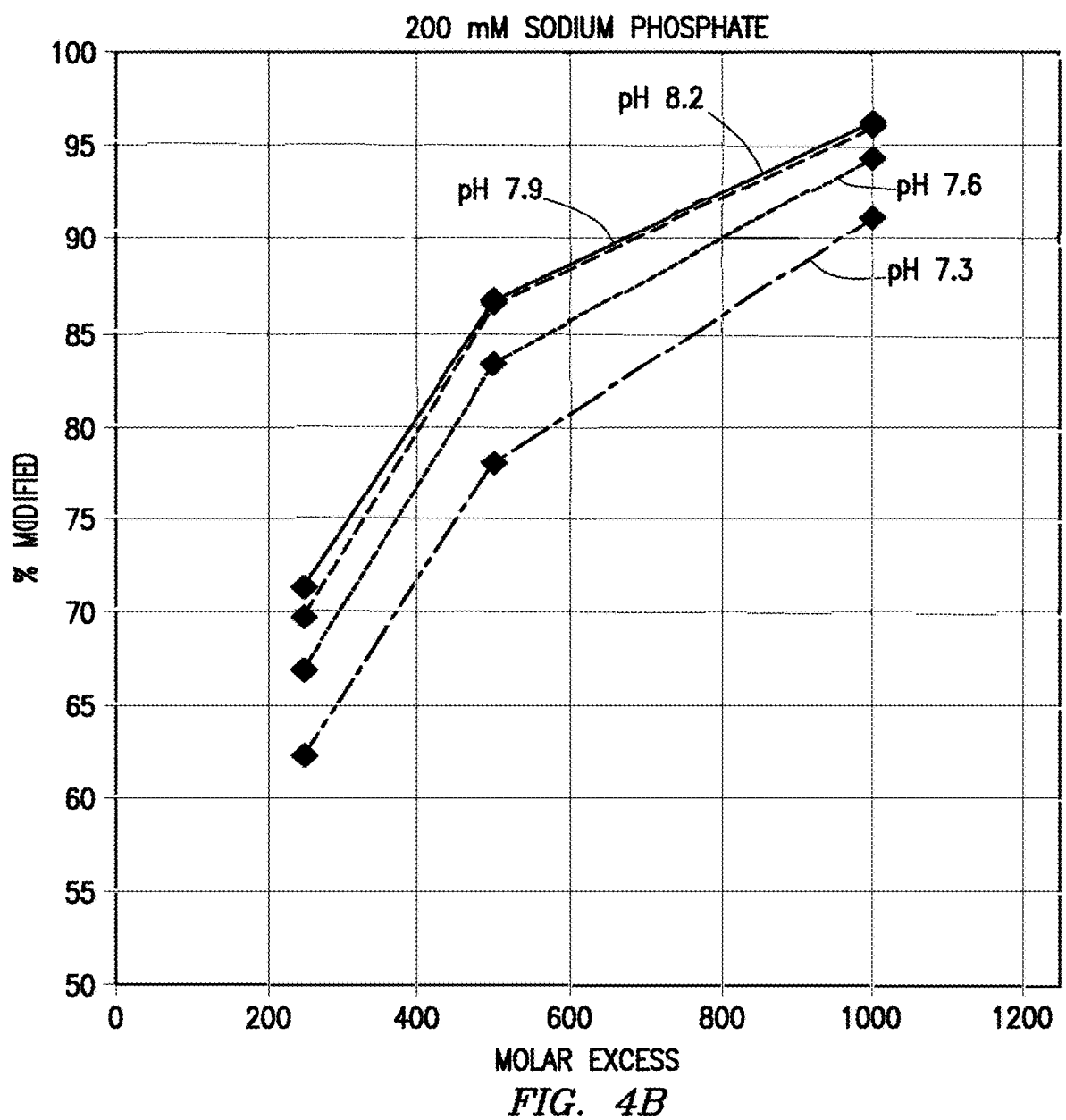
Figure 4C:
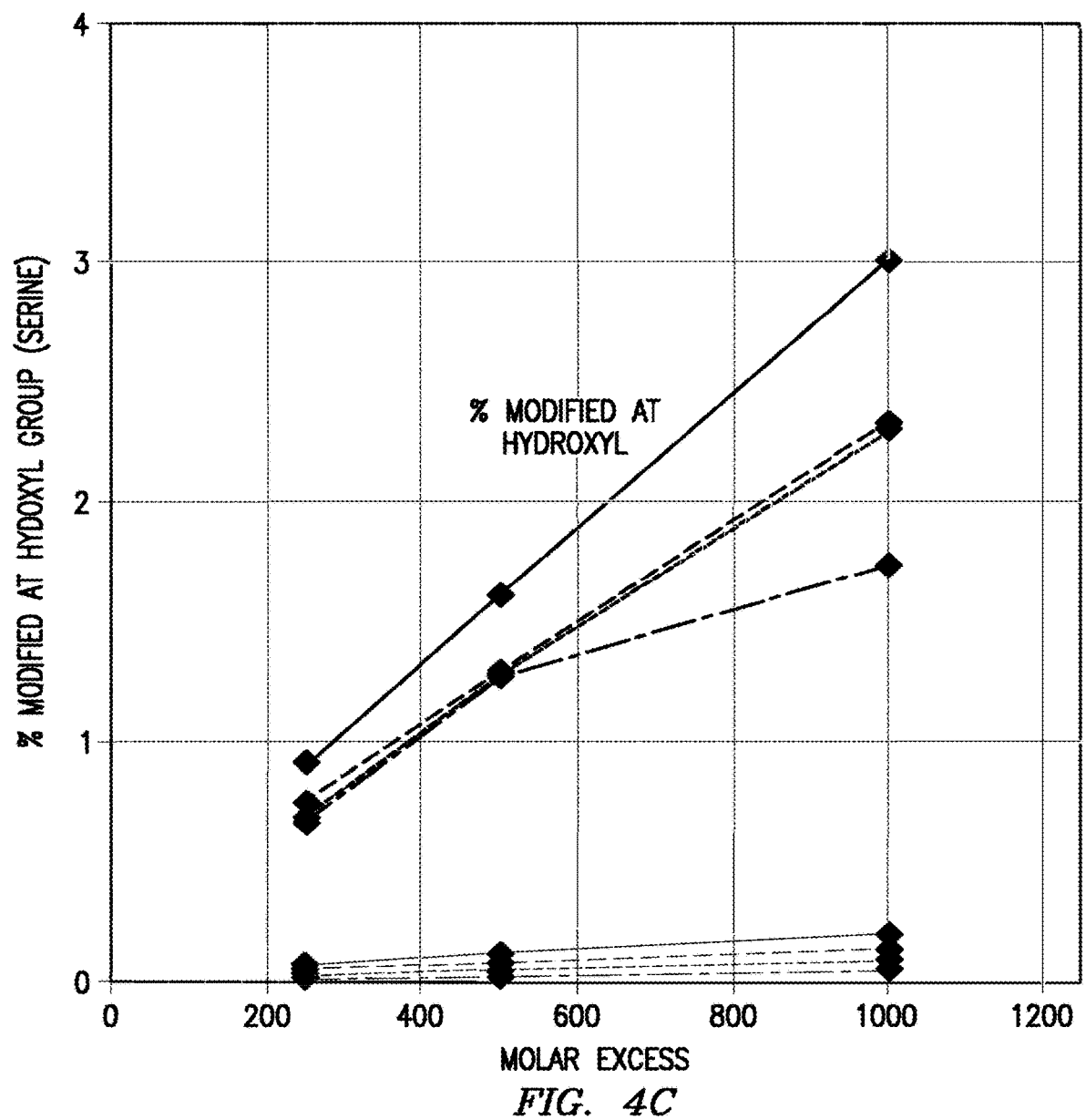
FIG. 4C shows the % of glycosylamines modified at the hydroxyl groups when the 200 mM sodium borate and 200 mM sodium phosphate buffers are used in the reaction mixture.
Figure 5A:
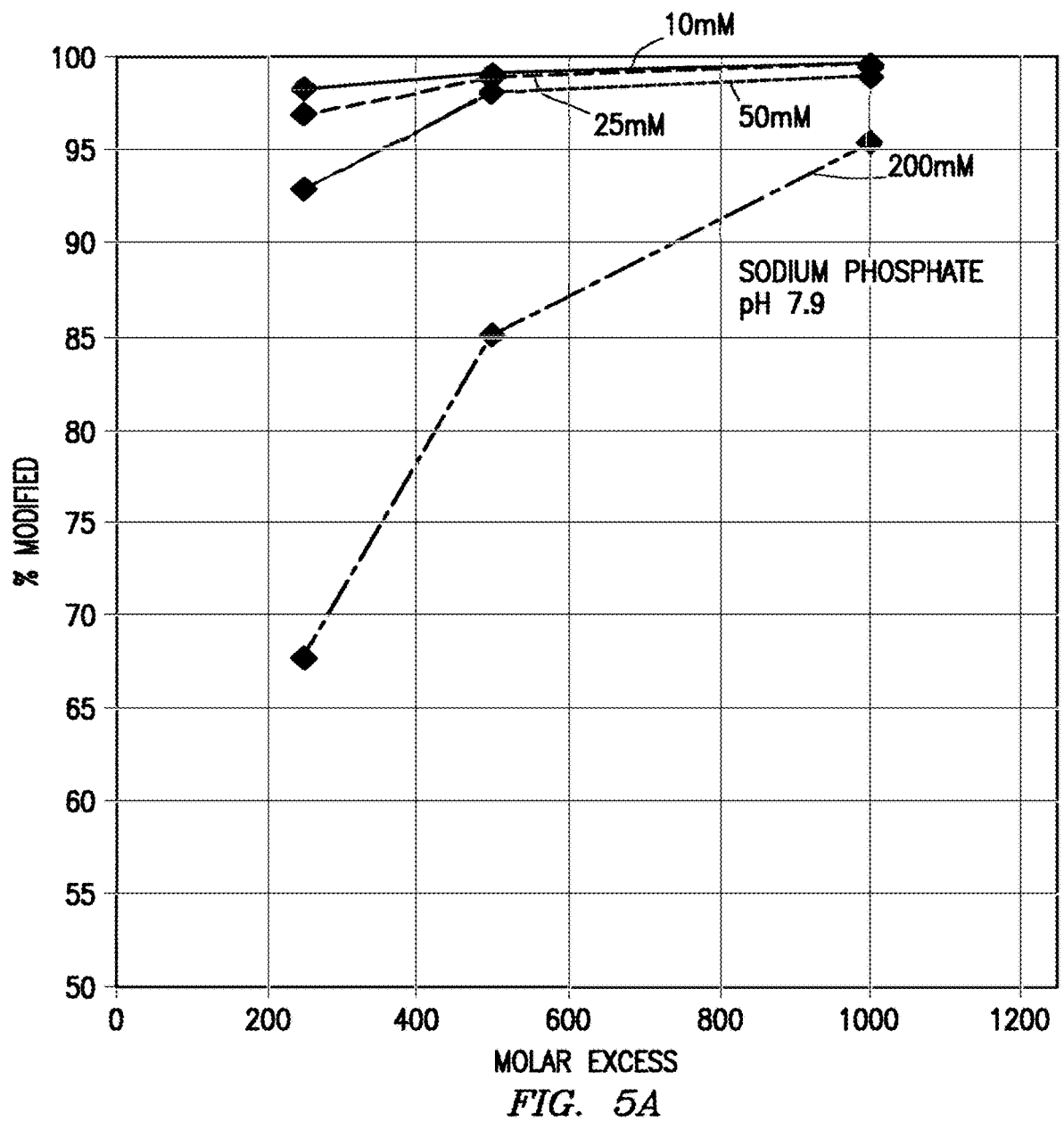
FIGS. 5A and 5B are graphs that show the effect of buffer concentration and ionic strength on the yield of amino-labeled and hydroxyl groups and on the reaction selectivity between amine and hydroxyl groups of Bradykinin.
Figure 5B:
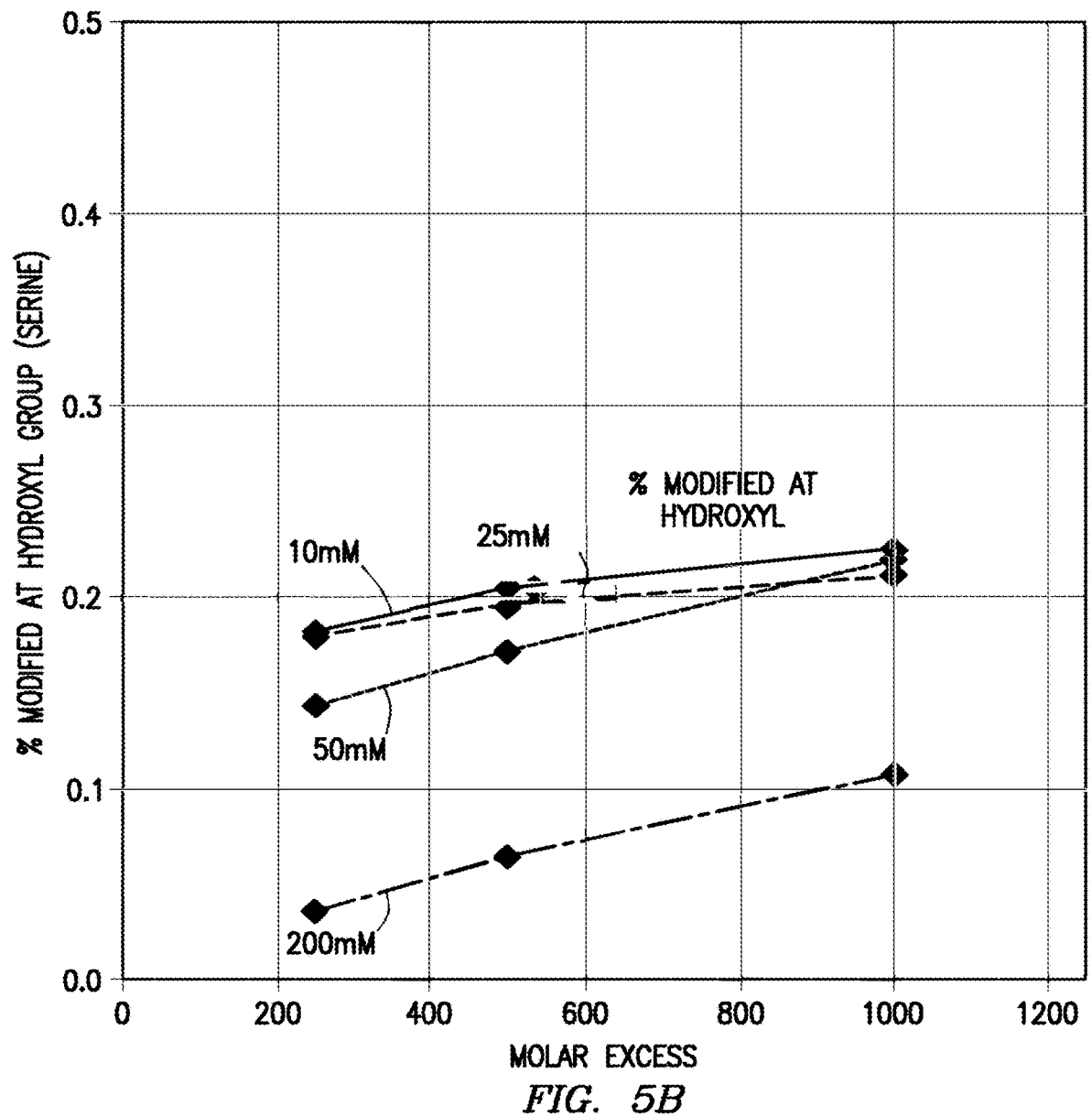

By measuring the % bradykinin population modified (with a single amine modification) together with bradykinin modified at its hydroxyl group (a single hydroxyl group modification or two site modification), we discovered reaction conditions in which the labeling yields and the selectivity of the reaction for the amine over the hydroxyl group are optimal. As shown in FIGS. 2 to 5, numerous plots of % modification versus molar excess of reagent are provided. Further, the discovery of optimal conditions for this type of reaction are exemplified including temperature as shown in FIG. 2, organic solvent composition as shown in FIG. 3, organic solvent concentration as shown in FIG. 3, buffer composition as shown in FIG. 4, pH as shown FIG. 4, and ionic strength as shown in FIG. 5.

In short, high labeling yields of derivatized compounds were achieved with minimal levels of overlabeling when: (1) temperature was at ambient to sub-ambient temperatures; (2) dimethylformamide (DMF) was used as an organic solvent; (3) DMF comprised no more than 20-30% of the reaction mixture; (4) a sodium phosphate solution buffer between pH 7.9 and pH 8.2 was employed, and (5) a phosphate concentration was maintained at ≤50 mM. Overlabeling is less than about 1 mole percent, more preferably about 0.0 to about 0.5 mole percent, and in some embodiments about 0.0 to about 0.2 percent. In addition, the buffer concentration can be between about 5 mM to about 1000 mM, or in some embodiments about 5 mM to about 200 mM or about 5 mM to about 100 mM or about 5 mM to 50 mM. A high yield of labeled glycosylamines can be achieved having a molar excess of the labeling reagent over modifiable amine in an amount ranging between about 10 to about 2000, or about 30 to about 1000, or about 40 to about 500; or about 50 to about 300. Furthermore, though not necessarily advantageous in terms of yield, an organic solvent has been shown useful for the solubilization of some labeling reagents such as Labeling Reagent-1. We further discovered that 20-30% DMF is sufficient to enhance solubility without significantly impacting the yield and selectivity of the labeling reaction (FIG. 3). For this reason, a reaction mixture comprised of 20-30% DMF is preferred.

As provided in FIG. 3, organic solvent composition and concentration for dimethyl sulfoxide (DMSO) and dimethylformamide (DMF) were tested as co-solvents for the labeling reactions. Both, DMSO and DMF, are polar aprotic solvents and have both large dielectric constants (>20) and large dipole moments. Other polar aprotic solvents include tetrahydrofuran (THF) and acetonitrile. With high polarity, these solvents dissolve charged species including various anions and nucleophiles such as CN(-) and HO(-). Without hydrogen bonding, the nucleophiles are relatively "free" in solution and more reactive. Hence, solvents particularly useful in the present methods include non-nucleophilic, polar aprotic solvents.

Generally, common characteristics of aprotic solvents include: (1) solvents that can accept hydrogen bonds, (2) solvents do not have acidic hydrogen centers (acetone and esters fail this criterion); and (3) solvents dissolve organic salts. Polar aprotic solvents are solvents that will dissolve many salts, but lack acidic hydrogen. This type of solvent often has an intermediate dielectric constant and polarity. However, as noted above, certain polar aprotic solvents have both high dielectric constants and high dipole moments, another example being acetonitrile ("MeCN") and HMPA (hexamethylphosphoramide).

Figure 6:
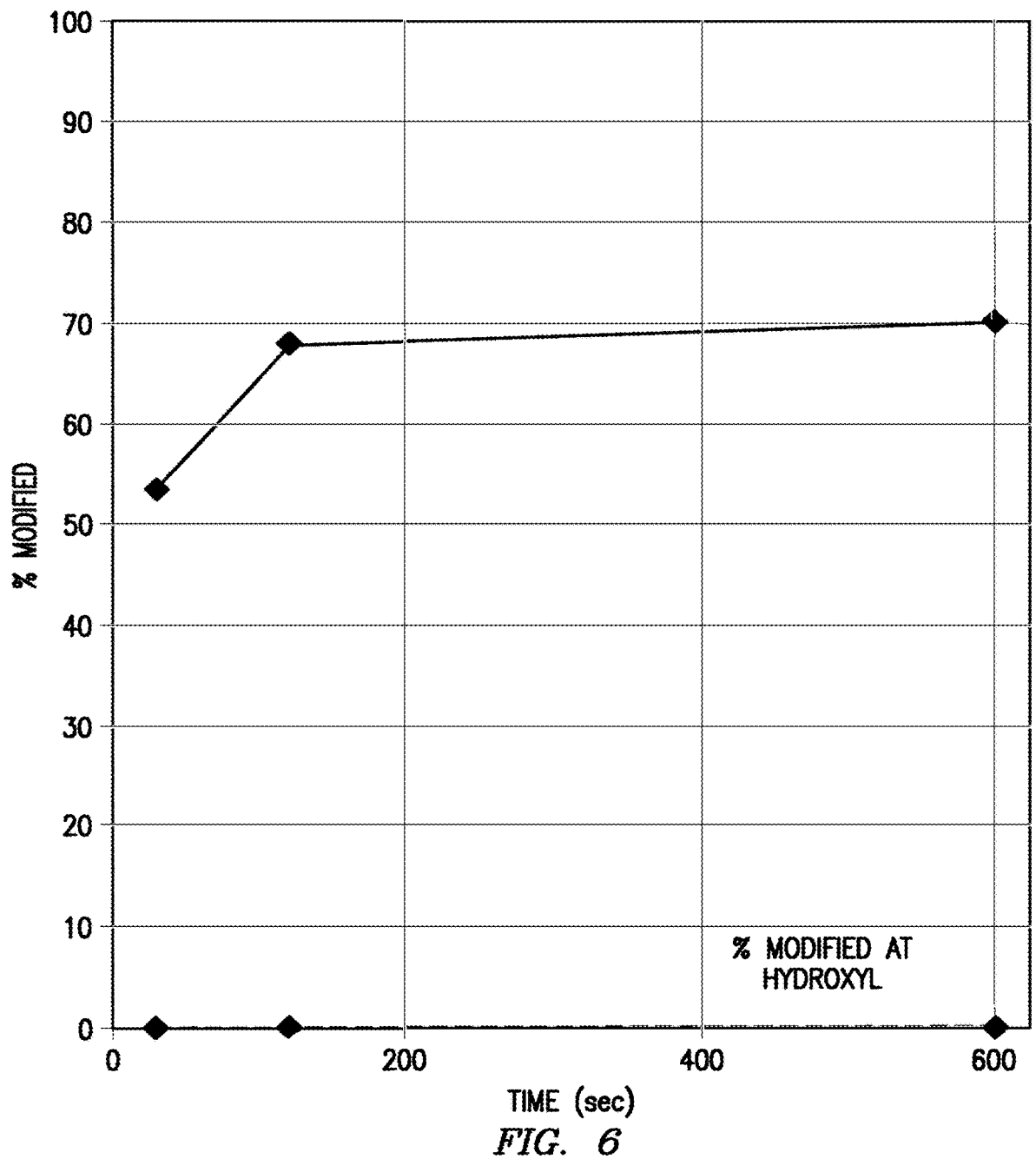
FIG. 6 is a graph that shows the effect of reaction time on the yield of amino-labeled groups and on the reaction selectivity between amine and hydroxyl groups of Bradykinin.

To define optimal reaction times and even more specifically, to define the time a reaction must be allowed to proceed before it is terminated, time course studies based on the Bradykinin assay were performed. FIG. 6 shows results from a time course experiment of reacting Labeling Reagent-4 with bradykinin for varying lengths of time before terminating the reaction by addition of diethylamine. As shown in FIG. 6, to obtain the optimum molar ratio of the tagging compound to the total primary amine concentration, the labeling reactions were performed using Labeling reagent-1 at concentrations of 500-fold, 400-fold, 300-fold, 200-fold and 100-fold molar excess. This time course shows that the reaction of an NHS carbamate under the outlined conditions is effectively complete after 120 seconds. For implementation with glycosylamine labeling, it is thus preferred that NHS carbamate reactions be allowed to proceed for between 2 and 10 minutes before additional sample processing is performed. Hence reaction times can range between about 10 seconds to about 30 minutes or in some embodiments, the reaction time is about 30 seconds to about 10 minutes or preferably, the reaction time is between about 2 minutes to about 5 minutes.

The above described methods have been employed to label N-glycans released from several monoclonal antibodies, including a murine IgG and a chimeric IgG (cetuximab) expressed from a murine Sp20 cell line. To prepare labeled N-glycans, glycoprotein samples are deglycosylated with peptide N-glycosidase F (PNGase F) and subsequently reacted with labeling reagent at room temperature. Labeling reagents are dissolved in anhydrous dimethylformamide (DMF) to a concentration of 127 mM. The deglycosylation mixture and the reagent solution are subsequently mixed in a 2.5:1 volumetric ratio to produce a reaction mixture comprised of approximately 36 mM labeling reagent and 4.8 μM released N-glycans (in the form of glycosylamines). Under these conditions, the glycosylamines are present in the reaction mixture along with any other amine species originating from the sample, most importantly proteinaceous amines of the precursor glycoprotein. Glycoproteins tend to contain many more proteinaceous amines (i.e. lysine residues) than N-glycan sites. Accordingly, the most abundant amines in the deglycosylation mixture will be proteinaceous amines.

We have further discovered that it is advantageous in terms of speed and reproducibility to purposely maintain the proteinaceous amines in the sample. Hence, higher concentrations of labeling reagent (i.e Labeling Reagent-1) can be added to the reaction mixture and in turn any otherwise unaccounted for amines and nucleophiles will have inconsequential effect on the yield of the labeling. The labeling of glycosylamines will, as a result, be more reproducible from sample-to-sample. In addition, the amount of labeling reagent can be more easily tuned for desired characteristics of amine modification. For instance, high yields of labeled glycosylamines can be obtained more easily with less concern of producing over-labeled glycan species.

Figure 7E:
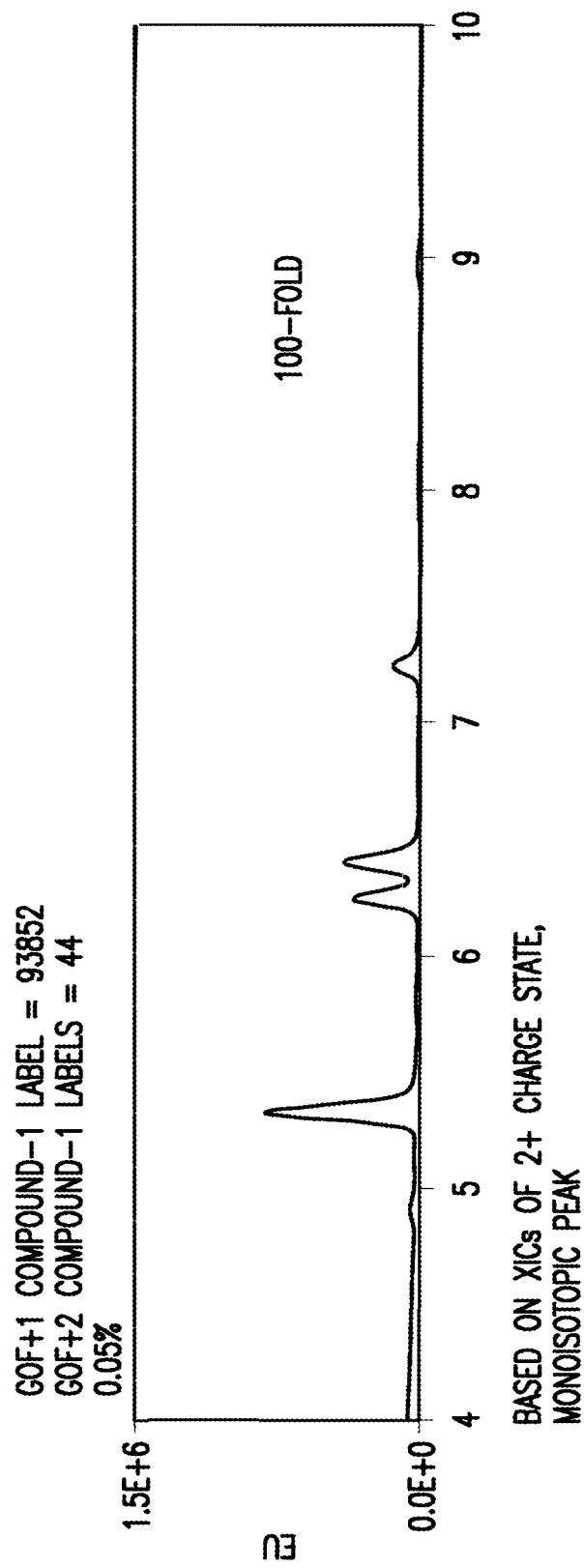

As an alternative, the labeling reaction (also referred to sometimes herein as "derivatization" or a "derivatization step") can be performed after depleting protein matter from the deglycosylation mixture. An IgG sample contains approximately 75 proteinaceous amines. Therefore, an IgG-based, released glycan mixture containing about 4.8 µM glycosylamines (2 glycans; one on each heavy chain) will contain at least 180 µm total primary amine composition. We discovered that under these conditions, the desired modification of a biological sample can be obtained via implementing a labeling reagent concentration of about 18 to about 180 mM that represents a range of about 100 to about 1000 fold molar excess of reagent over the total primary amine concentration. Conditions employing at least about a 200-fold molar excess are preferred in order to produce optimal labeling yields and relatively low levels of over-labeled glycans (≤0.24%). (FIG. 7)

Generally, labeling reactions are allowed to proceed for a minimum of about 5 minutes. Yet the tagging reaction can occur in a shorter time (i.e., seconds). By adding a quenching solution, the labeling reaction is terminated. The quenching solution contains about 5:5:90 (v/v/v) mixture of ethylene diamine/purified water/acetonitrile. By adding the quenching solution, the labeling reaction is terminated by adding significant concentrations of amine (>100 mM) to scavenge remaining, unreacted labeling reagent. The quenching solution also shifts the pH of the reaction mixture from a pH of about 6.5 to about 9 to a pH greater than 10. A shift to a basic pH ensures that labeled glycosylamines as well as reaction by-products, which can include urea-linked molecules, remain soluble. The high pH afforded by the addition of the quenching solution deprotonates the proton affinity/charge tag group of the label, thus enhancing solubility in high organic/low polarity solutions. This facilitates sample preparation procedures which rely on the polarity of glycans, as is the case when HILIC-based SPE is used to enrich labeled glycans from labeling reaction mixtures. Yu, Y. et al., *A Rapid Sample Preparation Method for Mass Spectrometric Characterization of N-Linked Glycans*, Rapid Commun Mass Spectrum 2005, 19 (16), 2331-6. If pH of the solution does not change, both reaction by-products and the labeled glycosylamines can co-precipitate, particularly when phosphate buffer is employed during the derivatization step.

Figure 8A:
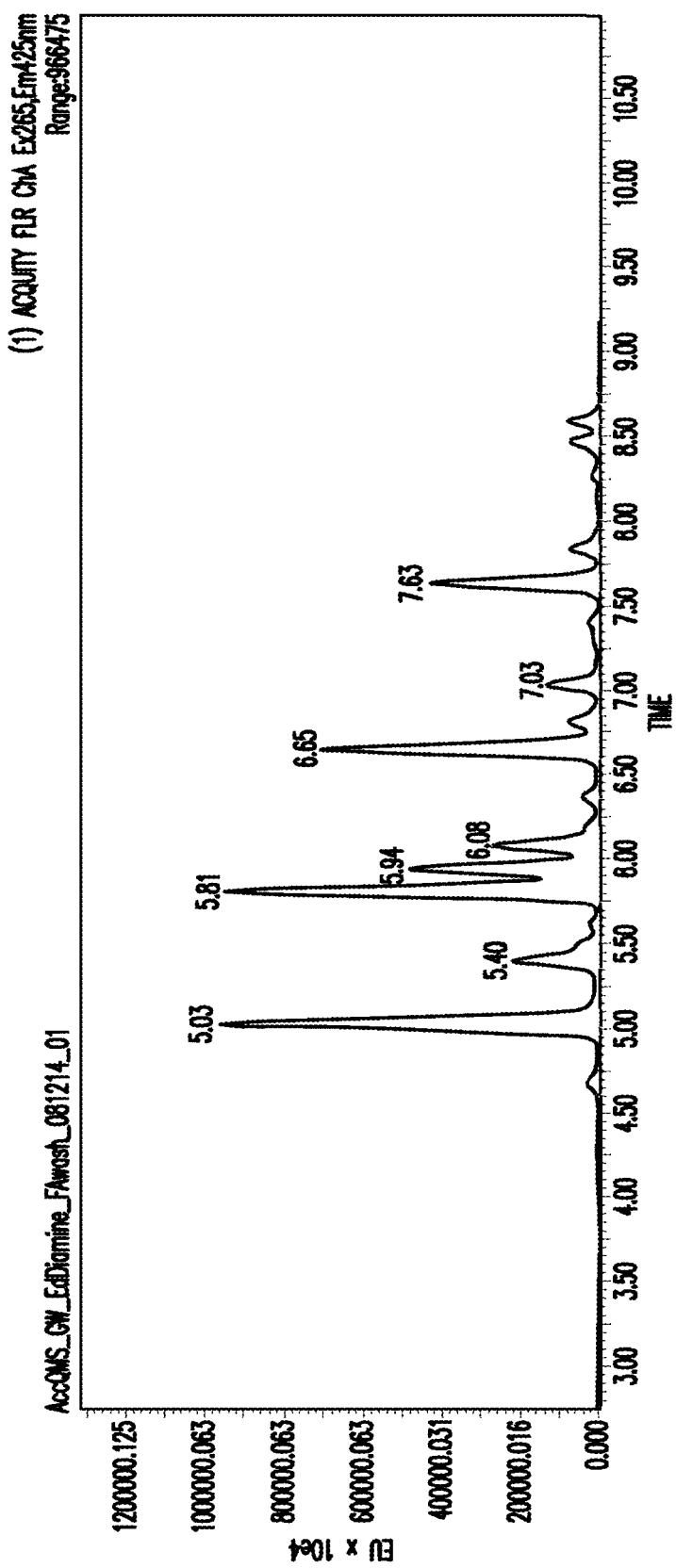
FIGS. 8A, 8B and 8C are chromatograms that show the results of fluorescently labeled N-glycosylamines released from pooled human IgG analyzed by LC with fluorescence detection and the effect of quenching solution composition on the fluorescence background levels.
Figure 8B:
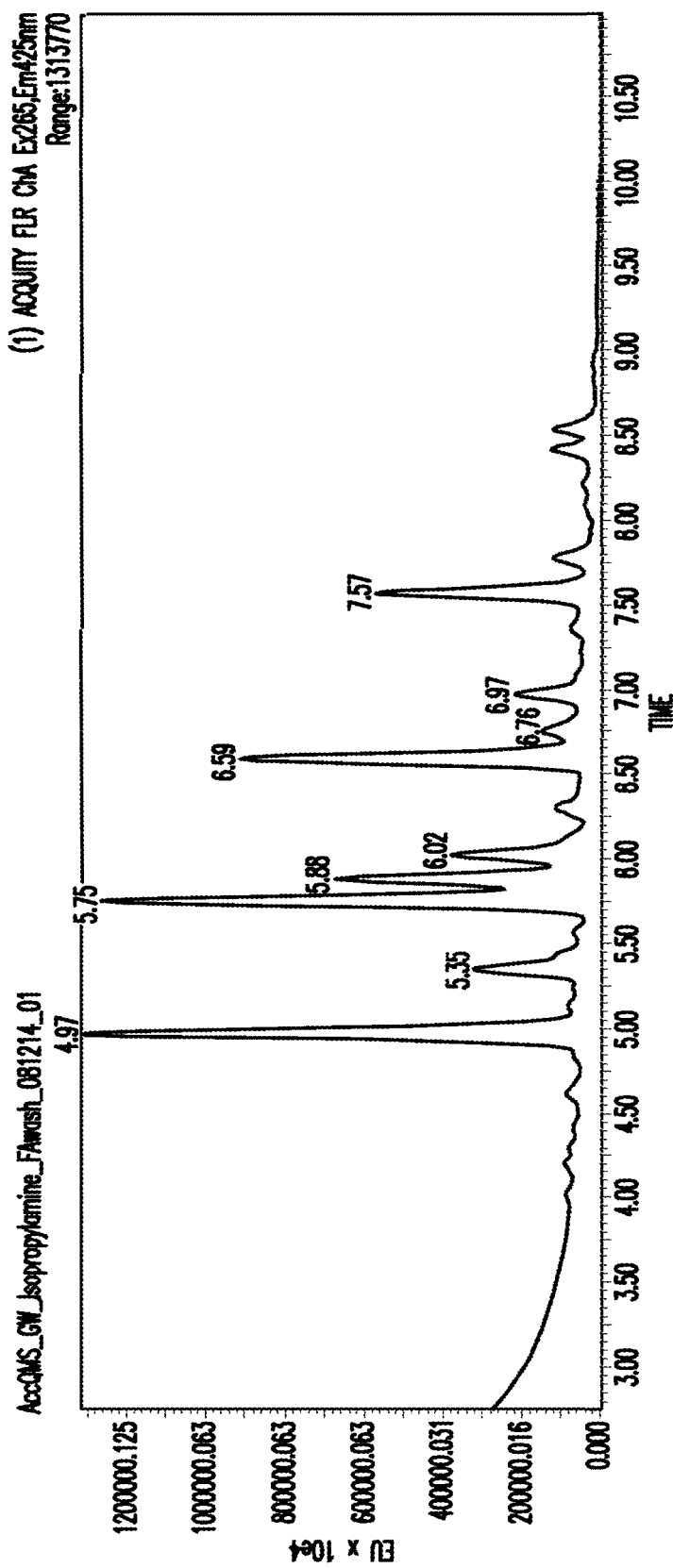
Figure 8C:
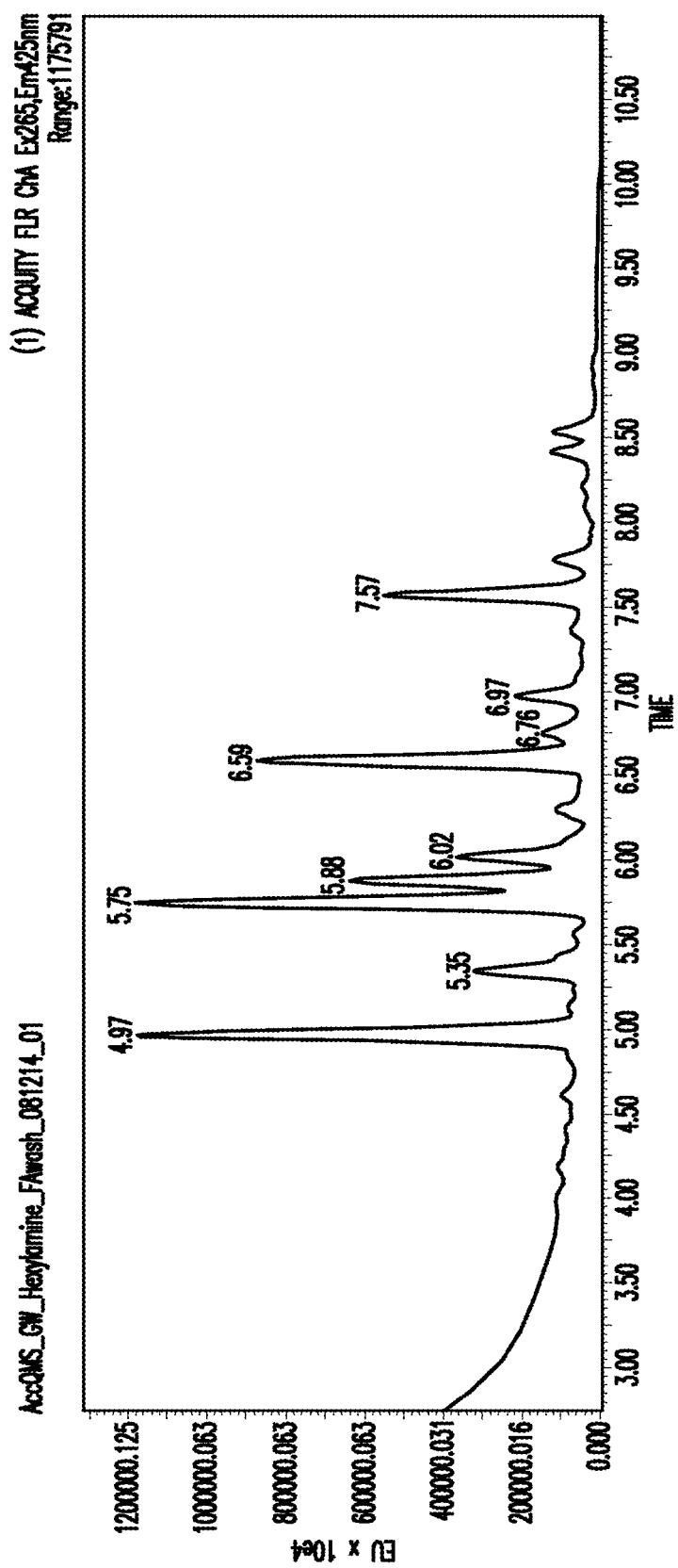

As described in Example II below, the quenching solution is added to the labeling reaction mixture at a volumetric ratio of about 9 to about 1 (9:1 (v/v)). Upon this step, the labeling reaction is terminated, and reaction products are dissolved in a solution compatible with HILIC SPE. The characteristics of the amine in the quenching solutions are important to this procedure. The amine should be significantly hydrophilic. Ethylene diamine is thus a preferred amine for the quenching solution. On the other hand, as shown by data of FIG. 8, other hydrophobic amines such as isopropyl amine and hexylamine have been tested and found to produce undesirable levels of background due to reaction byproducts when samples are analyzed by LC with fluorescence detection.

To separate the derivatized glycosylamines, a hydrophilic SPE sorbent, such as Waters Sep-Pak Aminopropyl, Waters Oasis HLB, or Waters Oasis WAX, can be conditioned for SPE and thereafter used to process the quenched, ACN-diluted sample. The Waters Sep-Pak Amino Propyl cartridge has a moderately polar, silica-based bonded phase with weakly basic surface. The sorbent can be used as a polar sorbent with different selectivity for acidic/basic analytes or as a weak anion exchanges in aqueous medium below pH 8. Applications for this type of cartridge include extraction of phenols and phenolic pigments, petroleum fractionation, saccharides and drugs and metabolites. The cartridges are designed to attach to pumps and syringes for reliable, positive-pressure flow to speed up the sample processing time. The cartridge also be fitted with removable reservoirs and used on vacuum-assisted flow devices and certain automated systems. SPE can likewise be performed with a miniaturized, 96-well formatted device.

After loading, the SPE sorbent can be washed to further facilitate removal of reaction by-products. Conditions to facilitate selectively enriching labeled glycosylamines from reaction by-products have been discovered. We discovered that an SPE wash step involving 1:14:85 (v/v/v) formic acid/water/acetonitrile is effective in reducing reaction by-products, which are manifest in LC chromatograms of obtained samples as detector saturating void peaks and sloping baselines. Other HILIC SPE wash solvents useful in this respect include 0.3:14.7:85 (v/v/v) phosphoric acid/water/acetonitrile. Useful HILIC SPE wash solvents can varying in acid composition, for example, from about 0.01 to about 10% when the organic solvent composition is about 50 to about 100% by volume, or from about 0.05 to about 5% when the organic solvent composition is about 60 to about 98% by volume, or from about 0.3 to about 3% when the organic solvent composition is about 70 to about 96%, and from about 0.1 to about 3% when the organic solvent composition is about 80 to about 95% by volume.

Figure 9C:
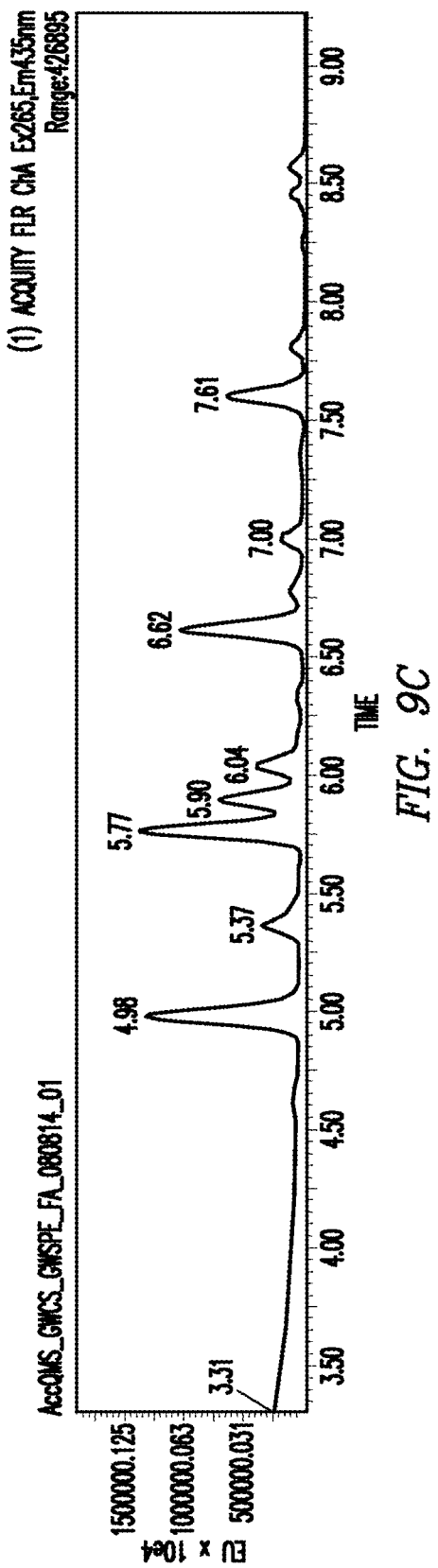

Several wash conditions have been employed during SPE. As shown in FIGS. 9A, 9B and 9C, wash conditions have an impact on the fluorescence chromatograms obtained for the labeled glycosylamines. The 1:14:85 (v/v/v) formic acid/water/acetonitrile is effective in reducing the fluorescence background and is also effective in shifting the pH of the loaded sample from high pH to low pH, which is an important consideration given that high pH is reported to induce epimerization of N-acetyl glucosamine residues into N-acetyl mannosamine. Liu, Y. et al., *Investigation of Sample Preparation Artifacts Formed During the Enzymatic Release of N-linked Glycans Prior to Analysis by Capillary Electrophoresis*, Anal Chem. 2009, 81 (16), 6823-9. Shifting the pH of the loaded sample quickly by washing with the acidic 1:14:85 (v/v/v) formic acid/water/acetonitrile wash solution also ensures that dissolution of silica-based SPE sorbents is minimized. Pettersson, S. W. et al., *Chemical Stability of Reversed Phase High Performance Liquid Chromatography Silica under Sodium Hydroxide Regeneration Conditions*, J Chromatogr A 2007, 1142 (1), 93-7.

As described herein, the high pH/low pH HILIC SPE process reduces the chromatographic background encountered during analysis of labeled glycosylamines. Nevertheless, the chromatographic background and peaks eluting near the void time of the HILIC column have been found to be further reduced in intensity by using HEPES (2-[4-(2-hydroxyethyl)piperazin-1-yl]ethanesulfonic acid) rather than phosphate for buffering the labeling reactions. This has resulted in SPE eluate with less intense chromatographic background. See, FIGS. 12A and 12B.

HEPES favorably altered the distribution, solubility, or SPE selectivity of reagent byproducts and can do so without the need for a quenching solution. Therefore, HEPES buffered solutions can be employed for deglycosylation and subsequent labeling of released N-glycosylamines. In addition, other buffering zwitterionic compounds, like HEPES, and having a pKa between about 7 to about 9 that are non-nucleophilic may be used including, but not limited to, ADA (N-(2-Acetamido)-2-iminodiacetic acid), BES (N,N-Bis(2-hydroxyethyl)-2-aminoethanesulfonic acid), BICINE (N,N-Bis(2-hydroxyethyl)glycine), DIPSO (3-(N,N-Bis[2-hydroxyethyl]amino)-2-hydroxypropanesulfonic acid), EPPS (4-(2-Hydroxyethyl)-1-piperazinepropanesulfonic acid), HEPBS (N-(2-Hydroxyethyl)piperazine-N'-(4-butanesulfonic acid)), MOBS (4-(N-Morpholino)butanesulfonic acid), MOPS (3-(N-Morpholino)propanesulfonic acid), MOPSO (3-(N-Morpholinyl)-2-hydroxypropanesulfonic acid), PIPES (1,4-Piperazinediethanesulfonic acid), POPSO (Piperazine-N,N'-bis(2-hydroxypropanesulfonic acid)). An ionization state of the buffering compound being neutral or positive, rather than negative, may further reduce the chromatographic background. Therefore, cationic, non-nucleophilic buffer compounds, such as tertiary amines: TEA (triethylammonia), BIS-TRIS (2,2-Bis(hydroxymethyl)-2,2',2"-nitrilotriethanol), BIS-TRIS propane (1,3-Bis[tris(hydroxymethyl)methylamino]propane) may be used.

In addition, online SPE can alternatively be used in place of offline SPE. Online SPE is typically performed in the form of one-dimensional trap-elute chromatography, wherein a so-called "trapping" column is paired via a fluidics switching mechanism with an analytical column. A trapping column is typically comprised of a large particle sorbent so that high linear velocity loading can be achieved while the effluent of the online SPE is diverted to waste. Samples are injected onto the trap/online SPE column and washed free of matrix components and contaminants. Subsequently, the effluent from the trap column is directed to an analytical column and a gradient is developed in order to elute and separate components of the sample. To assist in achieving optimal chromatography, the stationary phase of the trapping column must exhibit lower retentivity than the stationary phase of the analytical column. This match between trapping and analytical columns ensures refocusing of analytes onto the analytical column. Gradient elution thereby renders a separation with resolution matching that otherwise obtained by injecting the analyte directly onto the analytical column. Trap-elute chromatography has been commonly implemented for reversed phase separations, but not for HILIC separations. As such, we have discovered HILIC stationary phase retentivity for a new type of analyte: glycans, including labeled glycans, glycosylamines, or labeled glycosylamines.

HILIC sorbents and stationary phases for optimal online SPE/trap-elute chromatography have also been discovered. In particular, we have found that a polymeric, hydrophilic-lipophilic balance (HLB) sorbent (Waters Oasis HLB) exhibits ideal glycan retentivity for a trapping stationary phase. Specifically, we discovered that Oasis HLB retains glycans at conditions of approximately 10:90 water/acetonitrile. Meanwhile, glycans begin to elute from Oasis HLB with aqueous strengths of 11 to 15% water. This HILIC retentivity is unique in that it is weaker by approximately 10% acetonitrile when compared to the retentivities of stationary phases commonly used in glycan HILIC chromatography, for instance amide-bonded or polyol (polyhydroxyl) bonded stationary phases. Oasis HLB is a polymeric sorbent comprised of not only apolar moieties but also a repeating hydrophilic, amide moiety. This construction provides it with the noted HILIC retentivity that has been found to be advantageous for trapping/online SPE columns.

More specifically, for online SPE of glycosylamines (glycans), an Oasis HLB trapping column (i.e. 2.1×30 mm Waters Oasis HLB, 20 μm particle diameter) can be paired with an analytical column packed with amide bonded organosilica particles (i.e. 2.1×50 mm, Waters Glycan BEH Amide 130 Å 1.7 μm). Glycans are loaded onto the online SPE/trapping column while effluent is diverted to waste by some fluidics mechanism. The labeled glycosylamines adsorb to the sorbent in the SPE column and are washed at a comparatively fast flow rate with high organic mobile phase, such as 88% ACN. The mobile phase composition also can be modified with an additive such as 12:88 (v/v) 1% strong ammonia solution in $H_2O$:ACN. Effluent from the Oasis HLB SPE column can be redirected toward the analytical HILIC column after the wash step. During the wash step, derivatization by-products and other components of the sample matrix are flushed to waste. Therefore, the wash is designed to prevent interference. In addition, by using online SPE, wash solutions are typically in contact with the sorbent for only short periods of time, further avoiding matrix interference. On line SPE also reduces the amount of time that an analyst must spend performing manual sample preparation techniques.

Chromatographic conditions such as those described in Example 2 and suitable for gradient elution of glycans are then employed to obtain a separation and chromatogram.

Example 1

Discovery of Conditions for Maximum Labeling Yield and Minimal Over-Labeled Species Labeling reagents (i.e. Labeling Reagents 1-4) were reacted with 10 μM bradykinin. Reactions were performed under varying conditions; all reactions were quenched by the addition of a solution of 5M diethylamine HCl (pH 9.8) so that the final diethylamine concentration was approximate 800 mM. Obtained reaction products were assayed by LC-UV-MS using a Waters ACQUITY UPLC H-Class Bio combined with a Waters Synapt G2-S. Samples were injected in a volume of 10 μL onto an ACQUITY UPLC CSH C18 C18, 130 Å, 1.7 μm, 2.1×50 mm column. Separations were performed at a temperature of 60° C. and a flow rate of 0.3 mL/min using quaternary gradients between mobile phases comprised of 0.1% TFA (v/v) in water, 0.1% TFA (v/v) in ACN, 0.1% FA (v/v) in ACN, and 0.1% FA (v/v) in ACN. Eluting species were detected by UV absorbance (10 Hz, 214 nm) and by electrospray ionization mass spectrometry (100-2000 m/z, 2 Hz). Data obtained by the above process are presented in FIGS. 2 through 6.

Waters ACQUITY UPLC H-Class Bio is a chromatography system engineered with a bio-inert flow path of non-stainless steel materials to keep large biomolecules intact and moving through chromatographic columns. It utilizes sub-2-μm hybrid particle chemistry specifically intended for the analysis of proteins, peptides, nucleic acids, and glycans. It has a flow-through-needle injector and a quaternary solvent delivery system providing capability to run multiple chromatographic modes that include, but are not limited to, reversed phase (RP), ion exchange (EX), size exclusion (SEC), or hydrophilic interaction (HILIC) chromatography. This chromatographic system uses multi-solvent blending allowing for binary, ternary, or quaternary gradient operations with optional addition of a six-port solvent select valve for extra solvents to be used. Additionally, this system allows the user to change the concentration of mobile phase modifier and the organic solvent. Instead of manually preparing solvent mixtures, this system makes blends from pure solvents and concentrated stocks on demand. It also provides for automatic adjustment and calculations of the proportions of buffer stocks required for the desired conditions when pH and ionic strength are specified by the user. Furthermore, the system reduces volumes and minimizes band broadening to preserve the high efficiency of separation. It uses ultra-low-dispersion detectors to maintain peak integrity that enable multiple detection requirements for biological applications. Additionally, the system uses a variety of heaters and multi-column managers (with column switching) that provide for low dispersion and exact temperature management for control of chromatographic selectivity and the highest retention time precision.

Waters ACQUITY UPLC H-Class Bio can be combined with Waters Synapt G2-Si high definition mass spectrometry. Waters Synapt G2-Si is a high definition mass spectrometry system that uses the collision cross section (CCS) properties of ions, through the use of T-Wave ion mobility to enhance the peak capacity, specificity and sensitivity of biomolecule analysis. Waters Synapt G2-Si is equipped with a larger ion sampling orifice, an enhanced vacuum pumping configuration and ion transfer optics. This dual-T-Wave, off-axis design transfers ions from the ion source to the quadrupole MS analyzer with high efficiency, at the same time ensuring undesirable neutral contaminants are filtered out. This increases MS ion intensities while minimizing background noise.

Waters ACQUITY UPLC CSH C18 (Phenyl-Hexyl and Fluoro-Phenyl) columns provide alternate selectivity compared to other reversed-phase UPLC columns. These columns use 15% carbon load, C18 chemistry, with a 2.1 mm inner diameter, 30 mm length, end-capped, providing spherical particle shape with hybrid particle substrate, such as hybrid organic/inorganic particles. They contain 130 Å pore size and low silanol activity and are capable to handle pH in the range from about pH 1 to about pH 11.

Example 2

Rapid Preparation of Labeled Glycosylamines Released from Pooled Human IgG and Murine IgG1

Samples of pooled human IgG (from serum) and murine IgG1 were prepared in a similar manner. A lyophilized sample of IgG was reconstituted in 50 mM sodium phosphate pH 7.9 and mixed with peptide N-glycosidase F (PNGase F, New England BioLabs, P0705). This mixture was prepared such that the IgG concentration was approximately 1 mg/mL and that the activity concentration of PNGase F was approximately 25 units/µL. Subsequently, this mixture was incubated at 37° C. for 1 hour, conditions which yielded complete deglycosylation of the Fc region of the murine IgG. Upon completion of the 1 hour incubation, the deglycosylation mixture was allowed to cool to room temperature and thereafter diluted with an equal volume of 50 mM sodium phosphate pH 7.9. Meanwhile, Labeling Reagent-1 was dissolved in anhydrous dimethylformamide (DMF) to a concentration of 127 mM (assuming Labeling Reagent-1 is purified as a 1:1 complex with NHS). The deglycosylation mixture and the reagent solution were subsequently mixed in a 2.5:1 volumetric ratio to produce a reaction mixture comprised of approximately 36 mM Labeling Reagent-1 and 4.8 µM released N-glycans (and a total primary amine concentration of 180 µM) and reaction by-products which include, but are not limited to, a compound corresponding to the amine hydrolysis product of the labeling reagent and the reaction product produced by this amine and the labeling reagent (i.e., a urea linked molecule).

The reaction was allowed to proceed for 5 minutes and was then terminated by addition of a quenching solution (5:5:95 (v/v/v) ethylene diamine/water/ACN). The quenching solution was added to the reaction mixture in a volumetric ratio of 9:1. The resulting quenched, ACN-diluted sample was thereafter subjected to SPE using a Waters Sep-Pak Aminopropyl µElution plate and vacuum driven SPE. Wells were first cleaned with water and then conditioned with 15:85 (v/v) water/ACN. Subsequently, quenched, ACN-diluted samples were loaded onto the wells. The adsorbed samples were thereafter washed with a solution comprised of 1:14:85 (v/v/v) formic acid/water/ACN. Lastly, enriched, labeled glycosylamines were eluted from the SPE sorbent using an eluent composed of 100 mM ammonium acetate (pH 7), 5% ACN. The obtained labeled, glycosylamines were either directly analyzed in the form of the SPE eluate or instead as dried (by centrifugal evaporation) and reconstituted samples.

Figure 10:
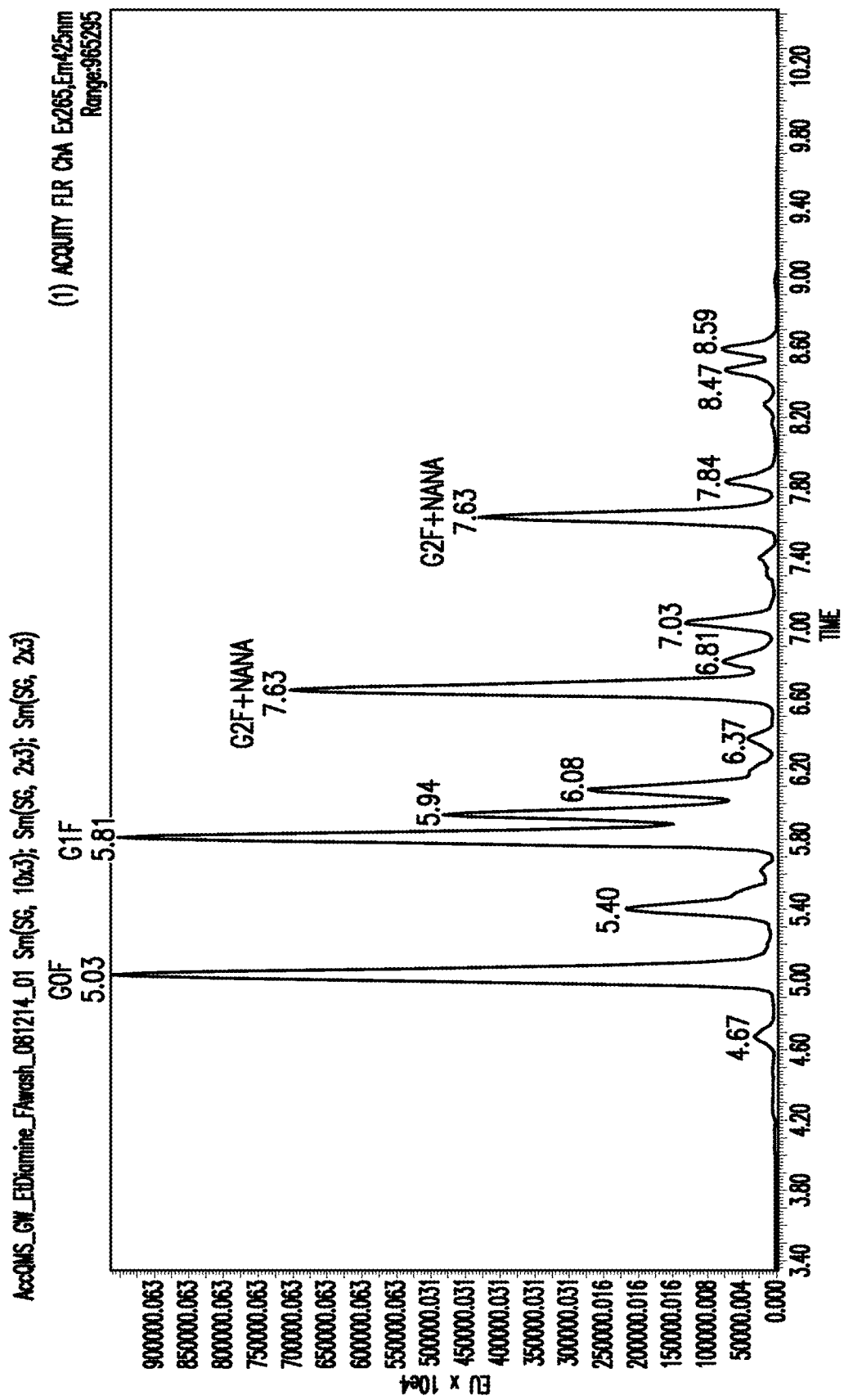
FIG. 10 is a fluorescence chromatogram obtained for pooled human IgG glysosylamines labeled with Labeling Reagent-1 as described in Example 2 using the methods described herein.

Analyses of the labeled glycosylamines were performed via HILIC separations and a combination of fluorescence and mass spectrometric detection (Waters ACQUITY UPLC H-Class Bio System paired with a Waters Synapt G2-S Mass Spectrometer). A 2.1×50 mm column packed with 1.7 µm amide-bonded organosilica particles was employed along with an aqueous mobile phase (Mobile Phase A) comprised of 50 mM ammonium formate (pH 4.5) and a mobile phase (Mobile Phase B) comprised of ACN. Aqueous samples were injected as 1 µL volumes and separated at a temperature of 60° C. according to the gradient Table 2. Labeled glycosylamines were detected using a fluorescence detector (5 Hz, Excitation λ=265 nm, Emission λ=425 nm) and by electrospray ionization mass spectrometry (600-2500 m/z, 1 Hz). FIG. 10 presents chromatographic data representative of samples resulting from this procedure.

TABLE 2

| Time (min) | Flow Rate (mL/min) | % A | % B | % C | % D | Curve |
|---|---|---|---|---|---|---|
| Initial | 0.4 | 25 | 75 | 0 | 0 | Initial |
| 15 | 0.4 | 52 | 48 | 0 | 0 | 6 |
| 15.5 | 0.2 | 100 | 0 | 0 | 0 | 6 |
| 16.5 | 0.2 | 100 | 0 | 0 | 0 | 6 |
| 17.7 | 0.2 | 25 | 75 | 0 | 0 | 6 |
| 19.2 | 0.4 | 25 | 75 | 0 | 0 | 6 |
| 21.7 | 0.4 | 25 | 75 | 0 | 0 | 6 |

Example 3

Rapid Preparation of Labeled Glycosylamines Released from Cetuximab

Figure 11A:
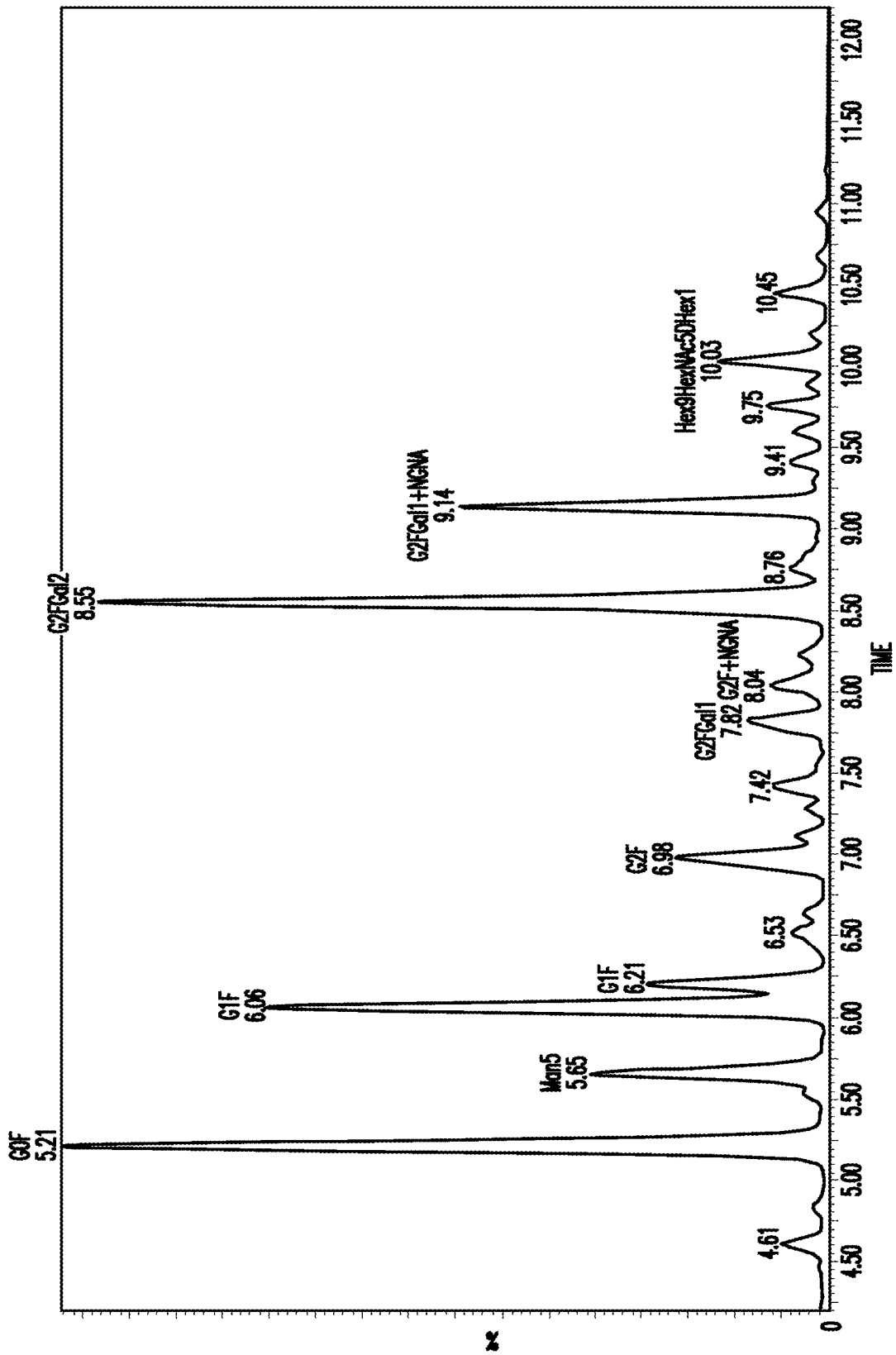
FIG. 11A is a fluorescence chromatogram obtained for cetuximab glycosylamines labeled with Labeling Reagent-1 as described in Example 3 using the methods described herein.
Figure 11B:
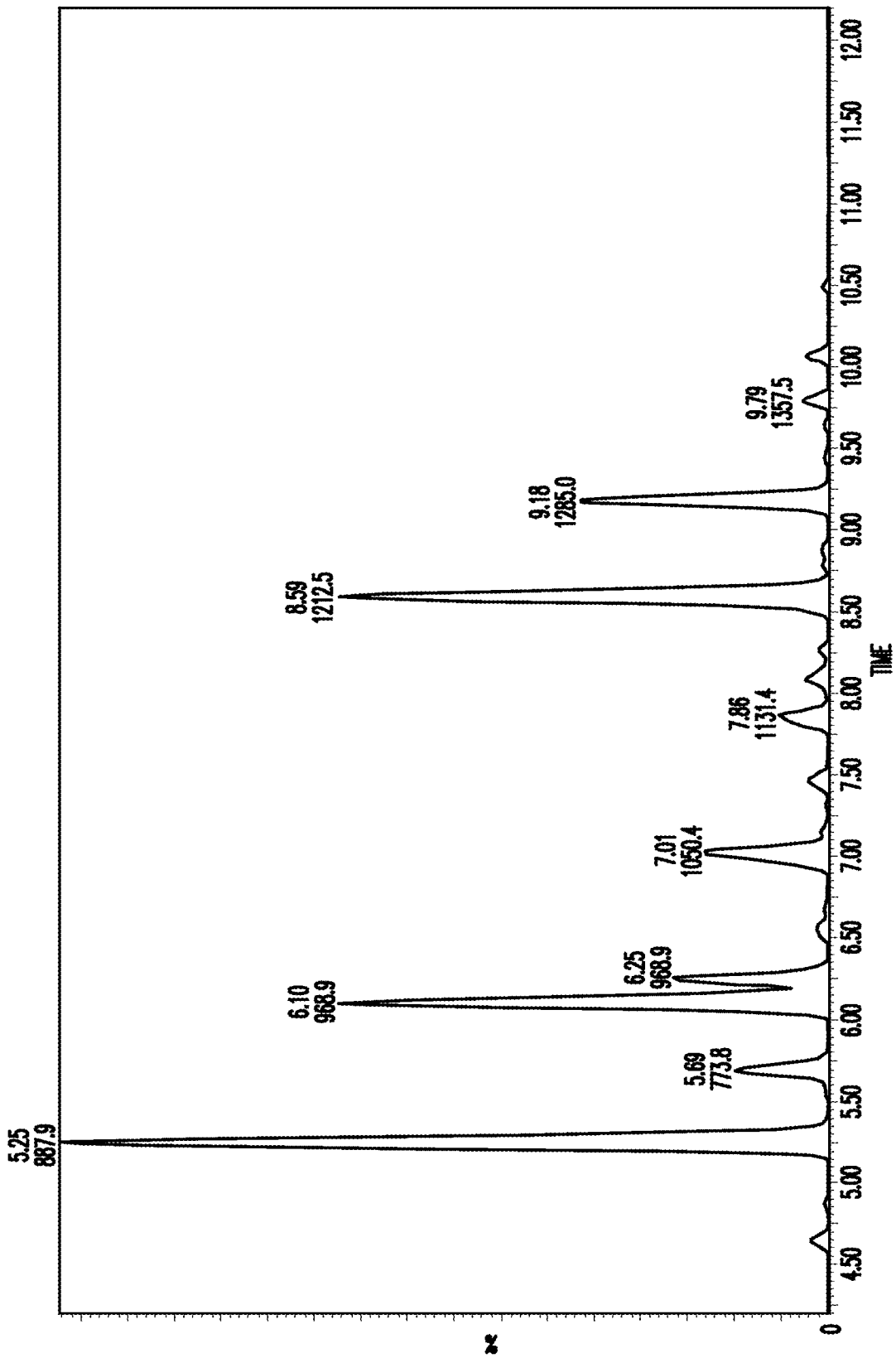
FIG. 11B is a base peak intensity chromatogram corresponding to FIG. 11A, as described in Example 3 using the methods described herein.

Labeled glycosylamines were prepared from cetuximab, a chimeric IgG1 expressed from murine Sp20 cells, using a procedure similar to that described in example 2, except that a unique deglycosylation process was employed. FIG. 11A and FIG. 11B present chromatographic data representative of cetuximab samples resulting from this procedure.

Example 4

Figure 13A:
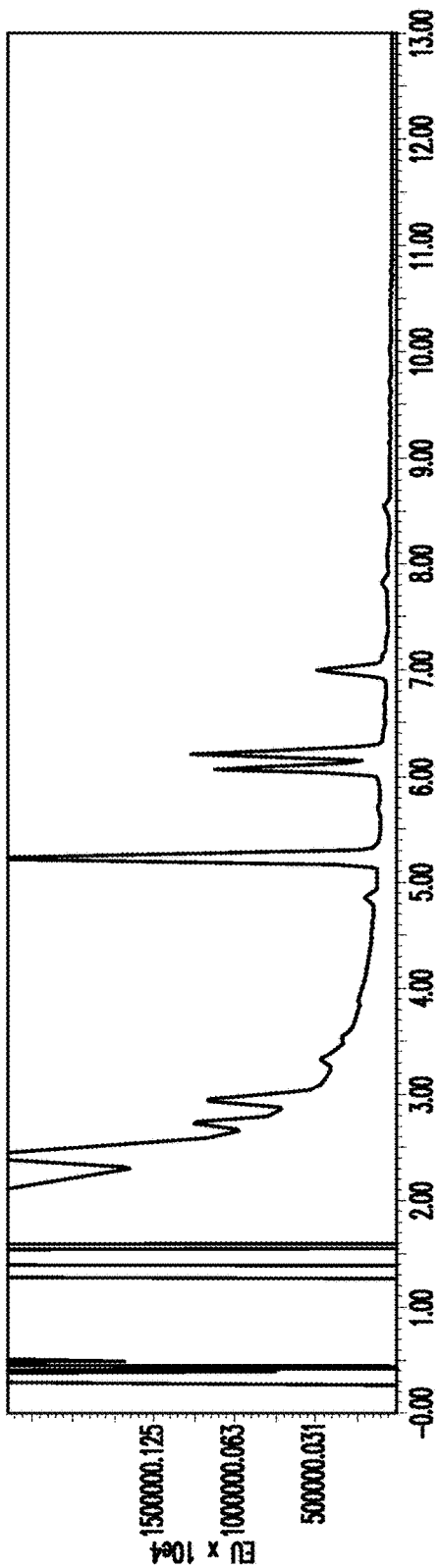
FIG. 13A is a HILIC fluorescence chromatogram obtained for anti-citrinin murine IgG1 glycosylamines labeled with Labeling Reagent-1 resulting from direct HILIC analysis of post-labeling reaction mixture.
Figure 13B:
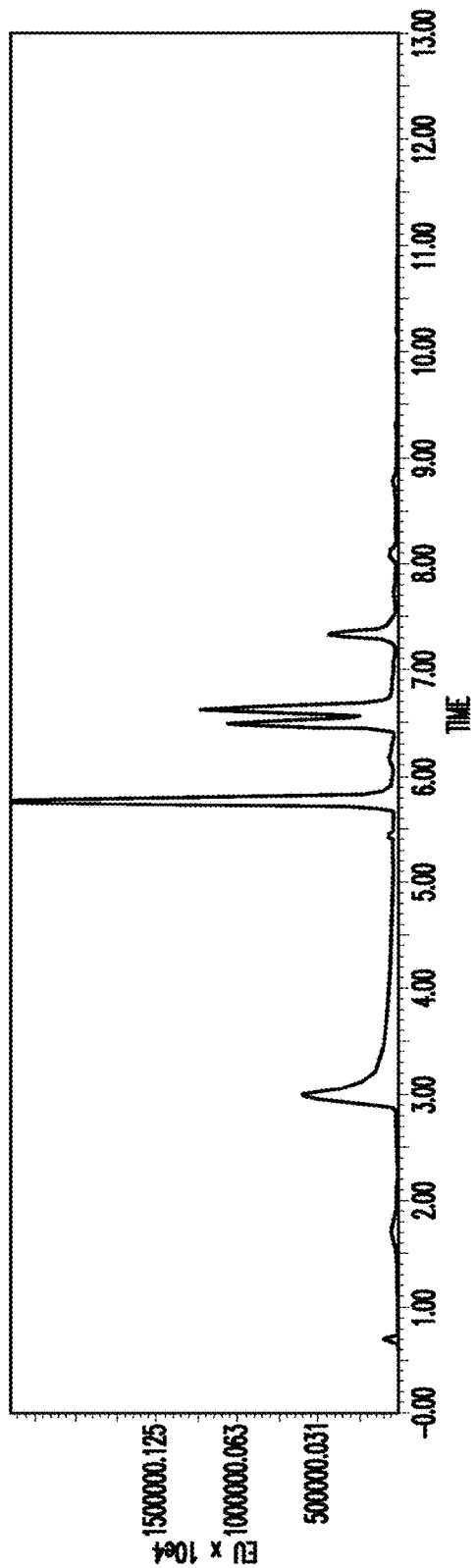
FIG. 13B is a HILIC fluorescence chromatogram obtained for anti-citrinin murine IgG1 glycosylamines labeled with Labeling Reagent-1 resulting from online SPE-HILIC analysis of post-labeling reaction mixture.
Figure 13C:
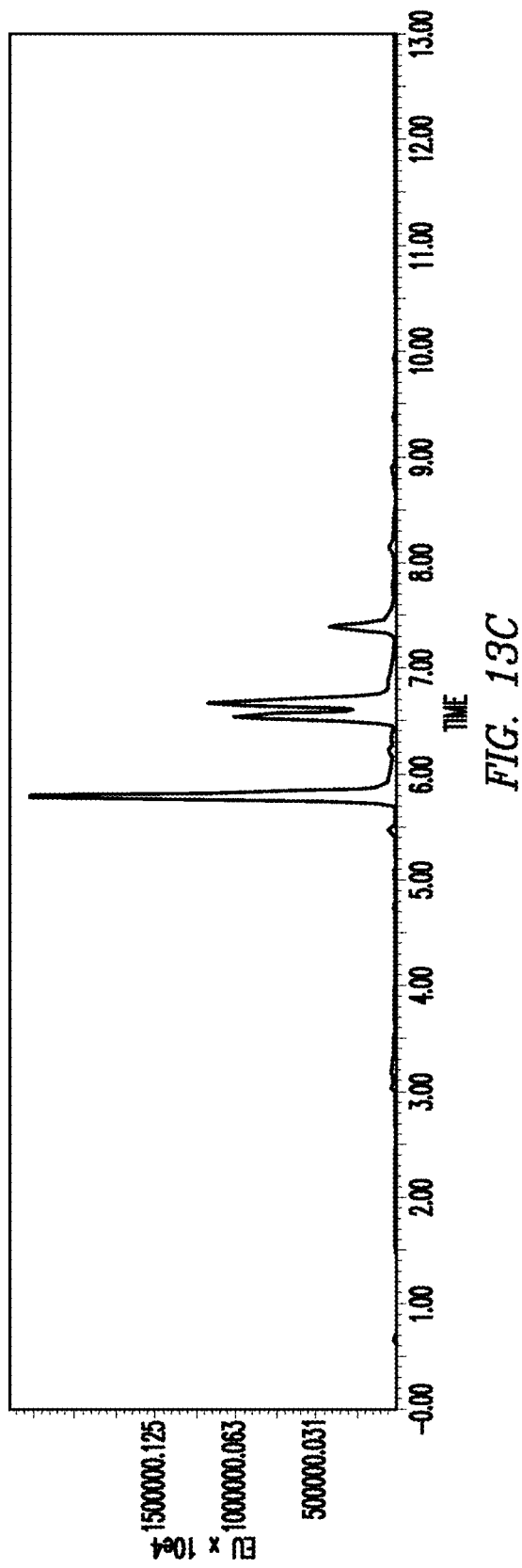
FIG. 13C is a HILIC fluorescence chromatogram obtained for anti-citrinin murine IgG1 glycosylamines labeled with Labeling Reagent-1 resulting from high pH/low pH online SPE-HILIC analysis of post-labeling reaction mixture.

FIGS. 13A, 13B and 13C provide example HILIC fluorescence chromatograms obtained for N-glycosylamines labeled with Labeling Reagent-1, purified by online SPE with Waters Oasis HLB, and then subsequently separated using an analytical column packed with amide-bonded stationary phase. Alternatives to Waters Oasis HLB can be used. Unbonded or diol-bonded sorbent constructed of silica or organosilica base particles have been found to exhibit retentivities that would make them useful trapping stationary phase alternatives.

More specifically, FIG. 13B is the chromatograph obtained for N-glycosylamines purified by online SPE having a mobile phase A of 50 mM Ammonium Formate at pH 4.5 and a mobile phase B of ACN. Furthermore, Table 3 immediately below is the SPE Gradient Table of the same. FIG. 13C is the chromatograph obtained for N-glycosylamines purified by online SPE having a mobile phase A of 50 mM Ammonium Formate at pH 4.5, a mobile phase B of ACN and a mobile phase C of 1% (v/v) ammonia hydroxide. Table 4 is the SPE Gradient Table for the same.

TABLE 3

Online SPE Gradient Table

| Time (min) | Flow Rate (mL/min) | % A | % B | % C | % D | Curve |
|---|---|---|---|---|---|---|
| Initial | 1.5 | 12 | 88 | 0 | 0 | Initial |
| 5 | 1.5 | 12 | 88 | 0 | 0 | 6 |

TABLE 4

Online SPE Grailient Table

| Time (min) | Flow Rate (mL/min) | % A | % B | % C | % D | Curve |
|---|---|---|---|---|---|---|
| Initial | 1.5 | 12 | 88 | 0 | 0 | Initial |
| 0.5 | 1.5 | 12 | 88 | 0 | 0 | 6 |
| 1 | 1.5 | 0 | 88 | 12 | 0 | 6 |
| 4 | 1.5 | 0 | 88 | 12 | 0 | 6 |
| 4.5 | 1.5 | 12 | 88 | 0 | 0 | 6 |
| 5 | 1.5 | 12 | 88 | 0 | 0 | 6 |

As described herein, variants of hydrophilic lipophilic balance polymeric sorbents can be used, including, but not limited to, Phenomenex Strata X (a functionalized polymeric sorbent containing N-Vinylpyrrolidone having multiple modes of retention for analyte-sorbent interaction), Thermo Hypersep PEP (cartridges packed with porous DVB material modified with urea functional groups), Agilent SampliQ OPT (packed with an amide modified divinyl benzene polymer resin), Waters Oasis WAX, Waters Oasis WCX, Waters Oasis MAX, and Waters Oasis MCX. Phenomenex Strata X sorbent is a polymer-based reversed phase functionalized sorbent with surface area of 800 sq. m/g targeted for neutral and aromatic analytes, providing retention of neutral, acidic, or basic compounds under aggressive, high organic wash conditions. This sorbent relies on three mechanisms of retention: pi-pi bonding, hydrogen bonding (dipole-dipole interactions), and hydrophobic interaction. This type of sorbent is pH resistant and can handle pH range from 0 to 14. Thermo HyperSep Retain PEP cartridges are packed with a porous polystyrene DVB material modified with urea functional groups which can provide recovery of polar and non-polar analytes. These columns provide sorbent with 30-50 µm particle size and 30 mg bed weight.

Waters Oasis sorbents are a family of SPE sorbents, currently sold under the tradename OASIS. These sorbents are stable at pH extremes and in wide ranges of solvents. These sorbents have good retention of polar compounds, and a relative hydrophobic retention capacity 3× higher than that of traditional silica-based SPE sorbents like $C_{18}$. Additional extraction products include products such as Waters Oasis HLB, a universal sorbent for acid, neutral and basic compounds. Oasis HLB is a hydrophilic-lipophilic-balanced, water-wettable, reversed-phase sorbent made from a specific ratio of two monomers, the hydrophilic N-vinylpyrrolidone and the lipophilic divinylbenzene. Waters Oasis WAX cartridges are a polymeric reversed-phase, weak anion exchange, water-wettable mixed-mode polymer sorbent that has been optimized for high selectivity of strong acidic compounds. Waters Oasis WCX (Weak Cation Exchange) is a mixed-mode, water-wettable SPE sorbent made of copolymer substrate that provides retention of all types of analytes, especially of strong bases (pKa>10) and quaternary amines. The retention mechanism is mixed mode, both ion-exchange and reversed-phase. Waters Oasis MAX (Mixed-Mode Anion Exchange) is a mixed-mode polymeric sorbent optimized to achieve higher selectivity and sensitivity for extracting acidic compounds (pKa<1) with anion-exchange groups. This sorbent is water-wettable. Waters Oasis MCX (Mixed-Mode Cation Exchange) is a mixed-mode polymeric sorbent optimized for the retention of basic compounds with pKa 2-10.

Example 5

HILIC-Fluorescence-ESI-MS (MS/MS) Analysis of Labeled N-Glycans

To evaluate response factors, labeled N-glycans were analyzed via HILIC separations combined with fluorescence and mass spectrometric detection using a UHPLC chromatograph (ACQUITY UPLC H-Class Bio, Waters, Milford, MA). Either a 2.1×50 mm or a 2.1×150 mm column packed with 1.7 µm amide-bonded organosilica particles (ACQUITY UPLC Glycan BEH Amide 130 Å, Waters, Milford, MA) was employed along with an aqueous mobile phase comprised of 50 mM ammonium formate (pH 4.4) and another of ACN. Samples were injected as 1 µL aqueous volumes or 10 µL ACN/DMF volumes and separated at 60° C. according to the gradients. Labeled N-glycans were detected using a fluorescence detector (5 Hz scan rate, Gain=1, ACQUITY UPLC FLR, Waters, Milford, MA) using the excitation and emission wavelengths. Eluting glycans were also detected by positive ion mode electrospray ionization mass spectrometry using an ion mobility capable QT of mass spectrometer (Synapt G2-S, Waters, Milford, MA) operating with a capillary voltage of 3.0 kV, source temperature of 120° C., desolvation temperature of 350° C., and sample cone voltage of 80 V. Mass spectra were acquired at a rate of 1 Hz with a resolution of approximately 20,000 over a range of 500-2500 m/z.

Table 5 below sets out the structures and abbreviations associated with the glycan labeling described in this example together with the reagent used.

TABLE 5

| Reagent Used | Glycan Labeled Structure | Reference Name for Labeled Glycan |
|---|---|---|
| RapiFluor-MS Labeling Reagent-1 | 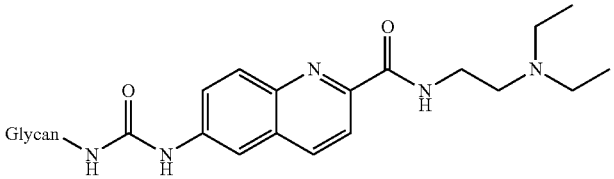 | RFMS Labeled |
| Instant AB or IAB Labeling Reagent-6 | 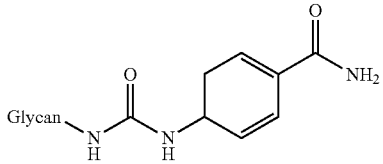 | IAB Labeled |
| 2-AB Labeling Reagent-7 | 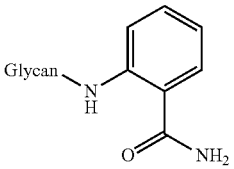 | 2-AB Labeled |
| Procainamide Labeling Reagent-5 | 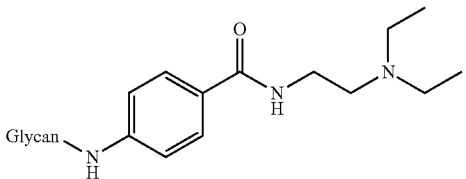 | Procainamide Labeled |

Results and Discussion

High Sensitivity Fluorescence and MS Detection

The sensitivity that RFMS labeling provides to N-glycan analyses has been evaluated. In particular, the response factors of RFMS labeled glycans have been benchmarked against response factors for glycans labeled with alternative reagents. The most closely related, commercially available alternative to RFMS is an NHS carbamate analog of aminobenzamide or IAB. Cook, K. S. et al., *Biologicals*, 40(2), 109-17 (2012).

Figure 14C:
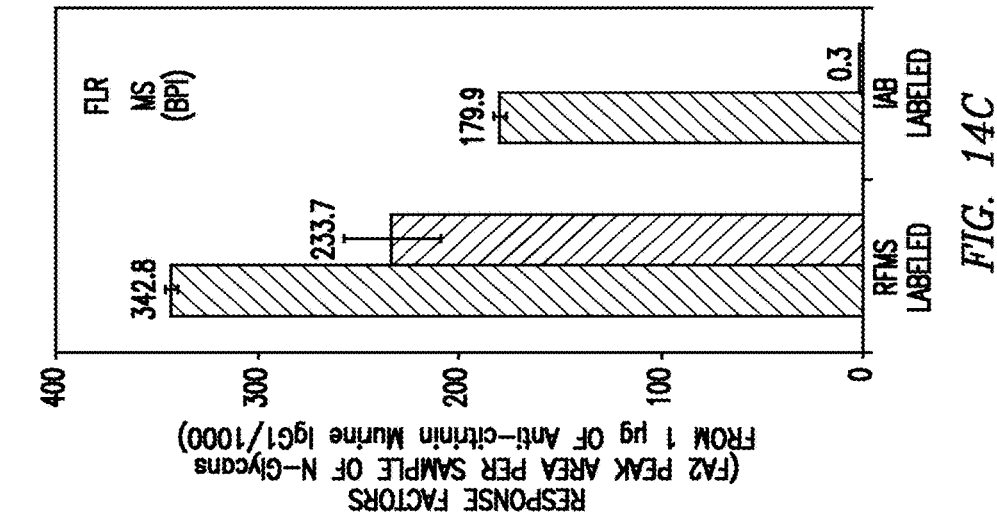
FIG. 14C shows response factors for RFMS and IAB labeled glycans.
Figure 14A:
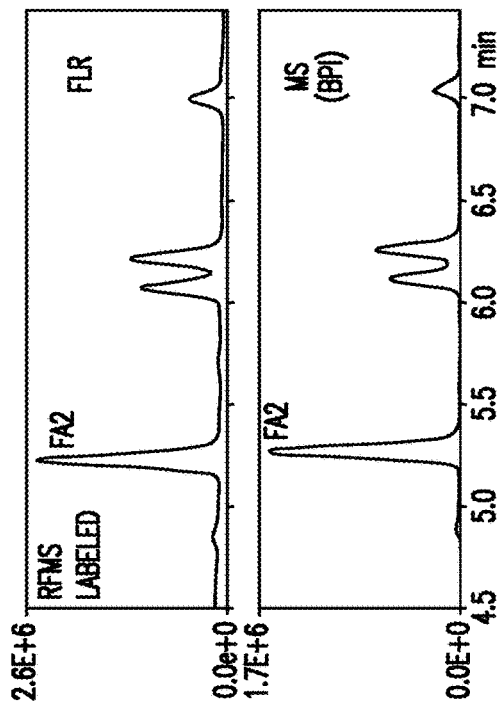
FIG. 14A is a HILIC-FLR-MS of RFMS labeled N-glycans from anti-citrinin murine IgG1.
Figure 14B:
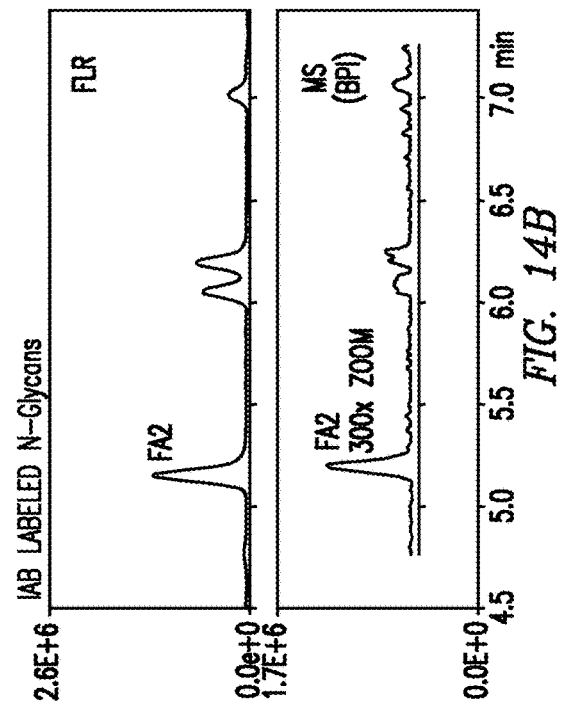
FIG. 14B is a HILIC-FLR-MS of IAB labeled N-glycans from anti-citrinin murine IgG1.

FIGS. 14A and 14B present HILIC fluorescence and base peak intensity (BPI) MS chromatograms for equivalent quantities of N-glycans released from a murine IgG1 monoclonal antibody and labeled with RFMS and IAB, respectively. Based on the observed chromatographic peak areas, response factors for fluorescence and MS detection were determined for the most abundant glycan in the IgG profile, the fucosylated, biantennary FA2 glycan (Oxford notation) (FIG. 14C). Harvey, D. et al, *Proteomics*, 9(15), 3796-801 (2009); Glycobase 3.2 http://glycobase.nibrt.ie (accessed 6 Jan. 2015).

FIG. 14A are the results of HILIC-FLR-MS of RFMS and FIG. 14B are the results of IAB labeled N-glycans from anti-citrinin murine IgG1. Fluorescence (FLR) chromatograms and base peak intensity (BPI) MS chromatograms are shown. Labeled glycans (from 0.4 μg glycoprotein, 1 μL aqueous injection) were separated using a 2.1×50 mm column packed with 1.7 μm amide bonded organosilica (130 Å) stationary phase. As shown in FIG. 14C, response factors for RFMS and IAB labeled glycans (measured as the FA2 peak area per sample of N-glycans resulting from 1 μg of anti-citrinin murine IgG1). Fluorescence (FLR) and MS (base peak intensity) response factors are shown, respectively. Analyses were performed in duplicate.

Our results for the FA2 glycan indicate that RFMS labeled glycans produce 2 times higher fluorescence signal and, more astoundingly, nearly 800 times greater MS signal than N-glycans labeled with IAB. In a similar fashion, RFMS labeling has also been compared to conventional 2-AB labeling. To draw such a comparison, N-glycans prepared from pooled human IgG with either RFMS or 2-AB were analyzed by HILIC-FLR-MS at equivalent mass loads (FIGS. 15A and 15B, respectively).

Figure 15C:
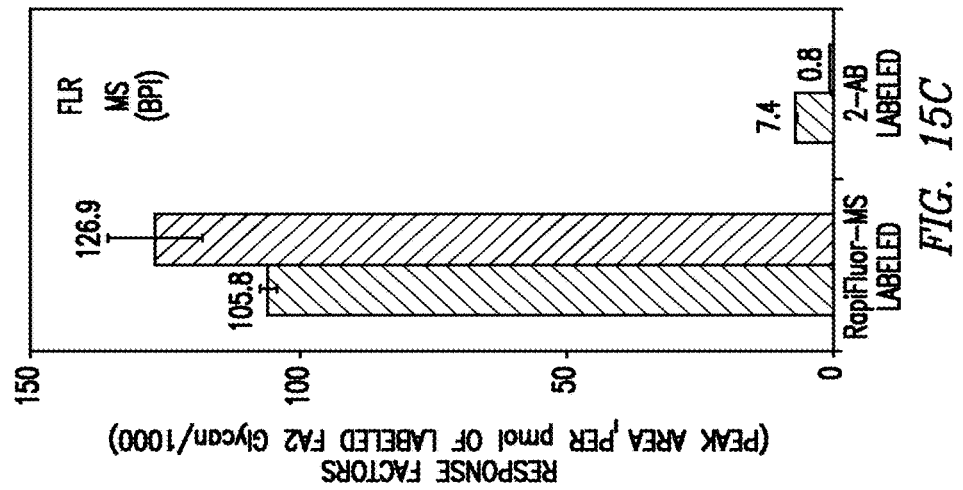
FIG. 15C shows response factors the RFMS and 2AB labeled glycans.
Figure 15A:
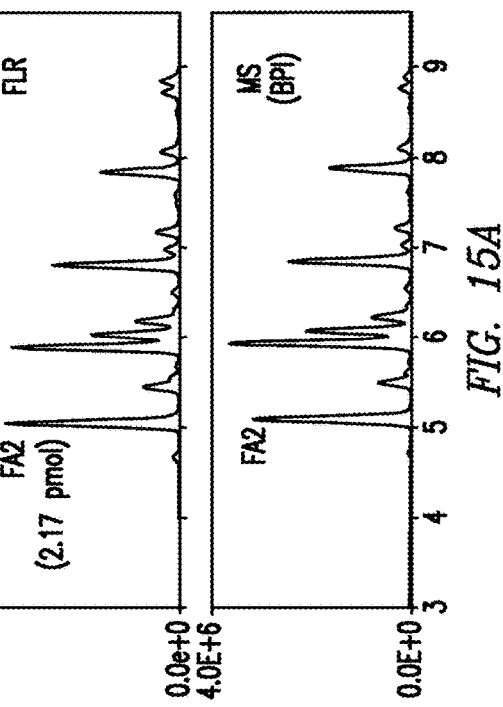
FIG. 15A is a HILIC-FLR-MS of RFMS labeled N-glycans from pooled Human IgG.
Figure 15B:
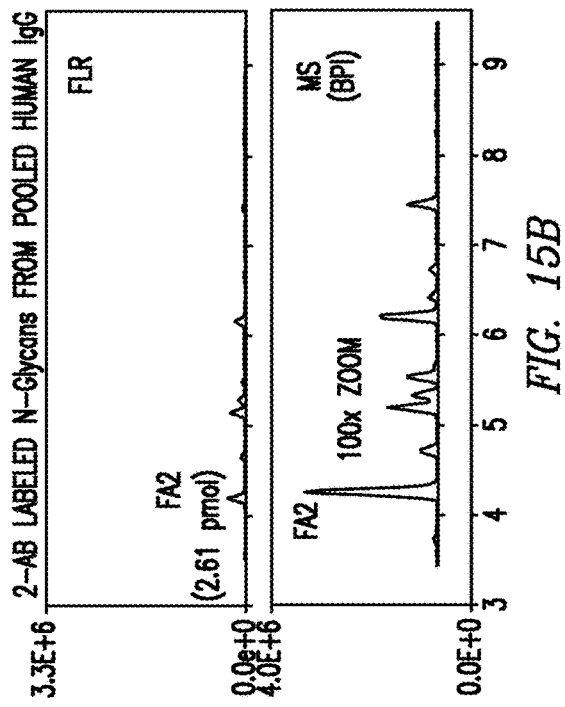
FIG. 15B is a HILIC-FLR-MS of 2AB labeled N-glycans from pooled Human IgG.

FIG. 15A depicts the HILIC-FLR-MS of RFMS and FIG. 15B depicts 2-AB Labeled N-Glycans from Pooled Human IgG. Fluorescence (FLR) chromatograms and base peak intensity (BPI) MS chromatograms are shown. Labeled glycans (~14 pmol total glycan, 1 μL aqueous injection) were separated using a 2.1×50 mm column packed with 1.7 μm amide-bonded organosilica (130 Å) stationary phase. The quantities of FA2 glycan were calibrated via two-point external calibrations with quantitative standards (RFMS derivatized propylamine and 2-AB labeled triacetylchitotriose). In FIG. 15C, response factors for RFMS and 2-AB labeled glycans (measured as the FA2 peak area per picomole of FA2 determined by the external calibration). Fluorescence (FLR) and MS (base peak intensity) response factors are shown, respectively. Analyses were performed in duplicate.

Given that rapid tagging and reductive amination are performed by significantly different procedures, external calibrations were established using quantitative standards in order to determine the amounts of FA2 glycan loaded and eluted from the HILIC column. Response factors calculated using these calibrated amounts of FA2 glycan are provided in FIG. 15C. It was determined that RFMS labeled glycans were detected with superior sensitivity, specifically with 14 times higher fluorescence and 160 times greater MS signal versus 2-AB labeled glycans.

Figure 16B:
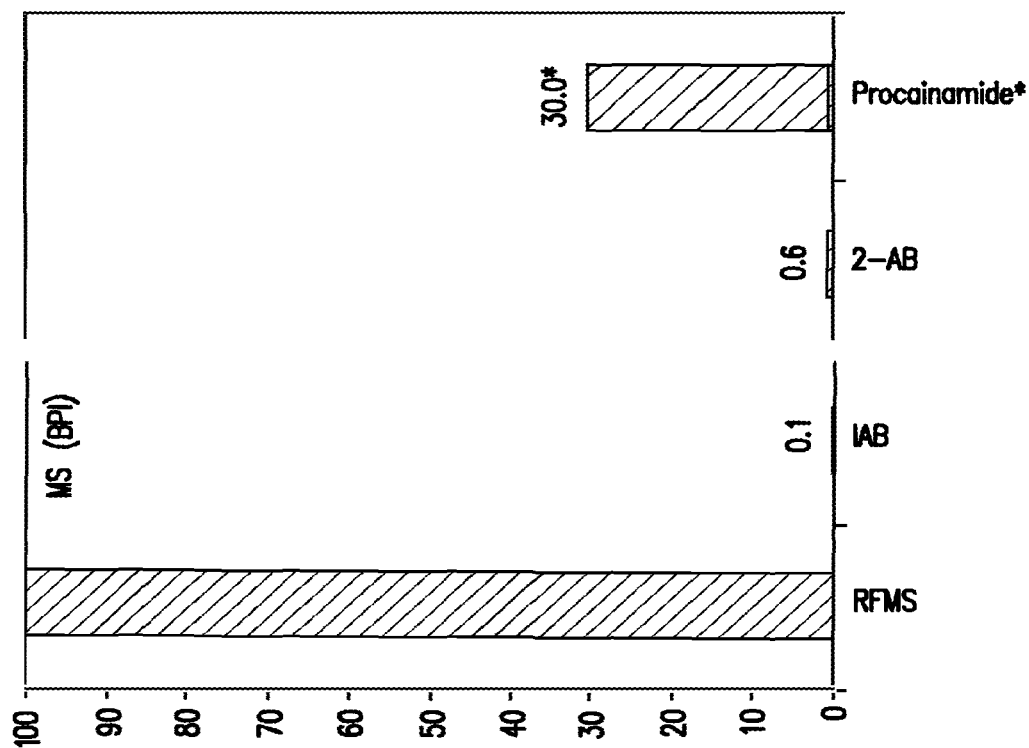
FIGS. 16A and 16B show the relative performance of glycan labels.
Figure 16A:
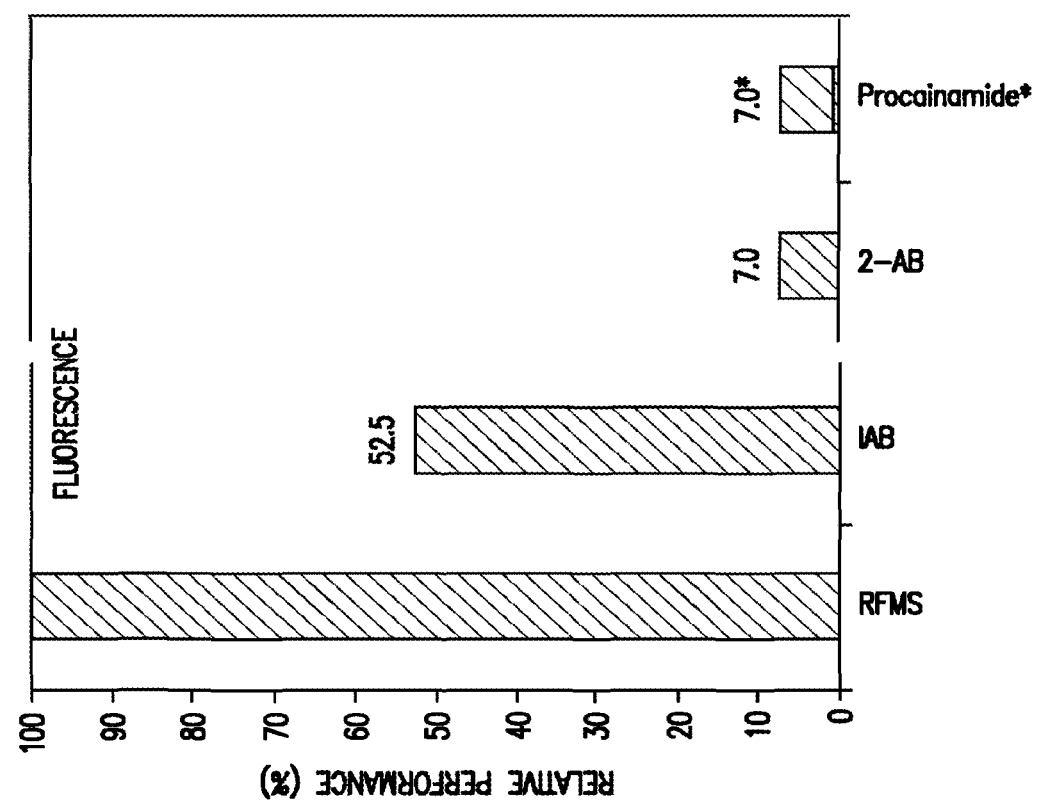

To summarize the above observations, we have plotted the response factors of IAB and 2-AB as percentages against the response factors of RFMS (FIG. 16). FIG. 16 shows the relative percent (%) performance of glycan labels. Response factors shown as percentages versus the fluorescence and MS response factors of RFMS labeled N-glycans. Comparative result extrapolated from a published comparison of N-glycans, wherein it was found that procainamide provided comparable fluorescence and up to 50 fold greater ESI-MS sensitivity when compared to 2-AB.

The gains in fluorescence and MS sensitivity are apparent in this plot, since it portrays response factors for IAB and 2-AB normalized to those for RFMS. In FIG. 16, the relative performance of reductive amination with another alternative labeling reagent, procainamide, is also provided. Procainamide is a chemical analog to aminobenzamide that has recently been shown to enhance the ionization of reductively aminated glycans when they are analyzed by HILIC-ESI(+)-MS. Previous studies have shown that procainamide labeled glycans yield comparable fluorescence signal and 10 to 50 times greater MS signal when compared to 2-AB labeled glycans, an observation corroborated by our own analyses of 2-AB and procainamide labeled N-glycans. Klapoetke, S. et al., J. Pharm Biomed Anal 53(3), 315-24 (2010). Compared to procainamide, RFMS is thus predicted to provide, at a minimum, a 3-fold gain in MS sensitivity. Since both these labels contain tertiary amine moiety, it is reasonable to suggest that the superior ionization of RFMS labeled glycans originates from the RFMS label being more hydrophobic than the procainamide label. Indeed, previous studies have shown that the addition of hydrophobic surface area to a glycan label leads to increased electrospray ionization. Walker, S. H. et al, J Am Soc Mass Spectrom 22(8), 1309-17 (2011); Bereman, M. S. et al., Chem Commun (Camb) 26 (2), 237-9 (2010). That the RFMS label has a strongly basic side chain in addition to a relatively hydrophobic core structure is therefore noteworthy. More notably, the above response factor data suggest that RFMS labeling provides unprecedented fluorescence and MS sensitivity for HILIC chromatographic profiling of N-glycans.

Example 6

Prophetic Method of Rapid Tagging of Amino Acids

Methods and reagents described herein can be used to perform rapid tagging of amino acids. Together with the appropriate buffer and diluent, pre-column derivatization and analysis of amino acids can be performed. To reconstitute a powder form of the derivatizing reagent, a vial of the reagent and diluent are heated on a heating block or other device set at 55° C. Reconstituted reagents are typically in the range of 10 mM in acetonitrile. Reconstituted reagent can be stored at room temperature typically for up to one week. However, alternative solvents and temperatures can be utilized. To derivatize a sample of amino acids, 60 µl of borate buffer is added to the reconstituted sample in a 6×50 mm sample tube and vortex. 20 µl of reconstituted reagent is then added and vortex immediately for several seconds. The mixture is allowed to incubate, typically for one to five minutes at room temperature. The contents of the tube are then transferred to a vial and sealed with a cap containing a silicone-lined septum. The vial is heated for 10 minutes at 55° C. Amino acid derivatives may be stored at room temperature for up to one week if tightly sealed and protected from evaporation.

Therefore, though designed for the preparation of glycosylamines, the described methods can be applied to amino acid labeling (regardless of the amino acid residues being free or constituents in proteins and peptides).

We claim:

1. A method of rapid derivatization of glycosylamines comprising the steps of:
    providing a biological sample comprising a glycoprotein;
    contacting the glycoprotein with an enzyme to produce a deglycosylation mixture; and
    mixing (a) a reagent solution comprising a labeling reagent selected from an N-hydroxysuccinimide ester reagent and an N-hydroxysuccinimide carbamate reagent combined with a polar aprotic, non-nucleophilic organic solvent, (b) the deglycosylation mixture, and (c) a buffer solution to produce a reaction mixture, the reaction mixture being formed under conditions in which protein matter has not been depleted from the deglycosylation mixture, the reaction mixture comprising a molar excess of labeling reagent, the reaction mixture having the labeling reagent, released glycosylamines, proteinacious amines comprising lysine residues, and derivatized glycosylamines wherein the derivatized glycosylamines are yielded between about 80 to about 100 percent and with overlabeling of glycosylamines in an amount of less than 0.2 mole percent.

2. The method of claim 1, further comprising the step of separating the derivatized glycosylamines by online solid phase extraction.

3. The method of claim 1, wherein the polar aprotic, non-nucleophilic organic solvent is selected from the group consisting of dimethylformamide (DMF), dimethyl sulfoxide (DMSO), and acetonitrile.

4. The method of claim 3, wherein the concentration of DMF in the reaction mixture is less than about 20 percent to about 30 percent by volume or DMSO in the reaction mixture is less than about 30 percent to about 50 percent.

5. The method of claim 3, further comprising adding a quenching solution to the reaction mixture, wherein the quenching solution comprises ethylene diamine and the pH of the reaction mixture shift to greater than about 10.

6. The method of claim 5, wherein the polar aprotic, non-nucleophilic organic solvent comprises acetonitrile and a ratio of ethylene diamine to water to acetonitrile is about 5 to about 90 by volume.

7. The method of claim 5, wherein the quenching solution is added to the reaction mixture about 2 to about 10 minutes after the deglycosylation mixture is mixed with the reagent solution.

8. The method of claim 1, wherein the deglycosylation mixture is mixed with the reagent solution in a volumetric ratio of about 2.5 to about 1.

9. The method of claim 1, wherein the reagent solution has a temperature maintained at about ambient temperature to sub-ambient temperatures.

10. The method of claim 1, further comprising the step of adding a buffer solution to the sample after the enzyme is combined with the biological sample.

11. The method of claim 10, wherein the buffer solution is HEPES or sodium phosphate.

12. The method of claim 11, wherein the buffer solution has a pH of about 7.9 to about 8.2 and a concentration of between about 5 mM to about 50 mM.

13. The method of claim 1, wherein the enzyme is peptide N-glycosidase F.

14. The method of claim 1, wherein the reaction mixture comprises a molar excess of labeling reagent in an amount of about 20 to 2000.

15. The method of claim 1, wherein labeling is allowed to proceed for between 2 and 10 minutes before additional sample processing is performed.

16. The method of claim 1, wherein the reagent solution has a temperature maintained at about ambient temperature to sub-ambient temperatures, wherein the reagent solution comprises dimethylformamide (DMF) in a concentration ranging from less than about 20 percent to about 30 percent by volume, wherein the buffer solution is selected from HEPES buffer and phosphate buffer, wherein the buffer solution has a pH of about 7.9 to about 8.2 and wherein the buffer solution has a concentration of between about 5 mM to about 50 mM.

\* \* \* \* \*